(12) United States Patent
Henry, Jr. et al.

(10) Patent No.: US 11,666,098 B2
(45) Date of Patent: Jun. 6, 2023

(54) CHARGING ACCESSORY DEVICE FOR AN AEROSOL DELIVERY DEVICE AND RELATED SYSTEM, METHOD, APPARATUS, AND COMPUTER PROGRAM PRODUCT FOR PROVIDING INTERACTIVE SERVICES FOR AEROSOL DELIVERY DEVICES

(71) Applicant: RAI Strategic Holdings Inc., Winston-Salem, NC (US)

(72) Inventors: Raymond Charles Henry, Jr., Green Cove Springs, FL (US); Michael Ryan Galloway, Winston-Salem, NC (US); Frederic Philippe Ampolini, Winston-Salem, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 597 days.

(21) Appl. No.: 16/399,364

(22) Filed: Apr. 30, 2019

(65) Prior Publication Data
US 2019/0255266 A1  Aug. 22, 2019

Related U.S. Application Data

(63) Continuation of application No. 14/175,391, filed on Feb. 7, 2014, now abandoned.

(51) Int. Cl.
*A61M 15/06* (2006.01)
*A24F 47/00* (2020.01)
(Continued)

(52) U.S. Cl.
CPC .............. *A24F 40/53* (2020.01); *A24F 40/65* (2020.01); *A24F 40/90* (2020.01); *A61M 15/06* (2013.01);
(Continued)

(58) Field of Classification Search
CPC .......... A61M 15/06; A61M 2205/3584; A61M 2205/502; A61M 2205/8206;
(Continued)

(56) References Cited

U.S. PATENT DOCUMENTS

| 1,771,366 A | 7/1930 | Wyss |
| 2,057,353 A | 10/1936 | Whittemore, Jr. |

(Continued)

FOREIGN PATENT DOCUMENTS

| AU | 276250 | 7/1965 |
| CA | 2 641 869 | 5/2010 |

(Continued)

OTHER PUBLICATIONS

"Innokin AIO PCC Review", Innokin AIO Review 2012 | Discount Code, <http://web.archive.org/web/20130203032101/http://www.ecigclick.co.uk/innokin-aio-pcc-review/>, Feb. 3, 2013, 6 pages.

(Continued)

*Primary Examiner* — Margaret M Luarca
(74) *Attorney, Agent, or Firm* — Womble Bond Dickinson (US) LLP

(57) ABSTRACT

The present disclosure relates to charging accessory device for the aerosol delivery device and related systems, methods, apparatuses, and computer program products for providing interactive services for aerosol delivery devices. For example, a method may include a computing device establishing communication with a charging accessory device for an aerosol delivery device; receiving usage data for the aerosol delivery device provided by the charging accessory device; generating social data based on the usage data; and sending the social data to a social networking service including a community of aerosol delivery device users.

24 Claims, 10 Drawing Sheets

(51) Int. Cl.
- *A24F 40/53* (2020.01)
- *G06Q 30/00* (2023.01)
- *G06Q 50/00* (2012.01)
- *A24F 40/65* (2020.01)
- *A24F 40/90* (2020.01)
- *H04L 67/01* (2022.01)
- *A24F 40/10* (2020.01)

(52) U.S. Cl.
CPC ............ *G06Q 30/00* (2013.01); *G06Q 50/01* (2013.01); *H04L 67/01* (2022.05); *A24F 40/10* (2020.01); *A61M 2205/123* (2013.01); *A61M 2205/13* (2013.01); *A61M 2205/3389* (2013.01); *A61M 2205/3584* (2013.01); *A61M 2205/502* (2013.01); *A61M 2205/52* (2013.01); *A61M 2205/8206* (2013.01)

(58) Field of Classification Search
CPC ...... A61M 2205/3389; A61M 2205/52; A61M 2205/123; A61M 2205/13; G06Q 30/00; H02J 2007/0096; H02J 2007/0098; H02J 7/0044; H02J 7/0027
See application file for complete search history.

(56) References Cited

U.S. PATENT DOCUMENTS

| | | |
|---|---|---|
| 2,104,266 A | 1/1938 | Mccormick |
| 2,805,669 A | 9/1957 | Merino |
| 3,200,819 A | 8/1965 | Gilbert |
| 3,316,919 A | 5/1967 | Green |
| 3,398,754 A | 8/1968 | Tughan |
| 3,419,015 A | 12/1968 | Wochnowski |
| 3,424,171 A | 1/1969 | Rooker |
| 3,476,118 A | 11/1969 | Luttich |
| 4,054,145 A | 10/1977 | Berndt et al. |
| 4,131,117 A | 12/1978 | Kite et al. |
| 4,150,677 A | 4/1979 | Osborne, Jr. et al. |
| 4,190,046 A | 2/1980 | Virag |
| 4,219,032 A | 8/1980 | Tabatznik et al. |
| 4,259,970 A | 4/1981 | Green, Jr. |
| 4,284,089 A | 8/1981 | Ray |
| 4,303,083 A | 12/1981 | Burruss, Jr. |
| 4,449,541 A | 5/1984 | Mays et al. |
| 4,506,682 A | 3/1985 | Muller |
| 4,635,651 A | 1/1987 | Jacobs |
| 4,674,519 A | 6/1987 | Keritsis et al. |
| 4,708,151 A | 11/1987 | Shelar |
| 4,714,082 A | 12/1987 | Banerjee et al. |
| 4,735,217 A | 4/1988 | Gerth et al. |
| 4,756,318 A | 7/1988 | Clearman et al. |
| 4,771,795 A | 9/1988 | White et al. |
| 4,776,353 A | 10/1988 | Lilja et al. |
| 4,793,365 A | 12/1988 | Sensabaugh, Jr. et al. |
| 4,800,903 A | 1/1989 | Ray et al. |
| 4,819,665 A | 4/1989 | Roberts et al. |
| 4,821,749 A | 4/1989 | Toft et al. |
| 4,830,028 A | 5/1989 | Lawson et al. |
| 4,836,224 A | 6/1989 | Lawson et al. |
| 4,836,225 A | 6/1989 | Sudoh |
| 4,848,374 A | 7/1989 | Chard et al. |
| 4,848,376 A | 7/1989 | Lilja et al. |
| 4,874,000 A | 10/1989 | Tamol et al. |
| 4,880,018 A | 11/1989 | Graves, Jr. et al. |
| 4,887,619 A | 12/1989 | Burcham, Jr. et al. |
| 4,907,606 A | 3/1990 | Lilja et al. |
| 4,913,168 A | 4/1990 | Potter et al. |
| 4,917,119 A | 4/1990 | Potter et al. |
| 4,917,128 A | 4/1990 | Clearman et al. |
| 4,922,901 A | 5/1990 | Brooks et al. |
| 4,924,888 A | 5/1990 | Perfetti et al. |
| 4,928,714 A | 5/1990 | Shannon |
| 4,938,236 A | 7/1990 | Banerjee et al. |
| 4,941,483 A | 7/1990 | Ridings et al. |
| 4,941,484 A | 7/1990 | Clapp et al. |
| 4,945,931 A | 8/1990 | Gori |
| 4,947,874 A | 8/1990 | Brooks et al. |
| 4,947,875 A | 8/1990 | Brooks et al. |
| 4,972,854 A | 11/1990 | Kiernan et al. |
| 4,972,855 A | 11/1990 | Kuriyama et al. |
| 4,986,286 A | 1/1991 | Roberts et al. |
| 4,987,906 A | 1/1991 | Young et al. |
| 5,005,593 A | 4/1991 | Fagg |
| 5,019,122 A | 5/1991 | Clearman et al. |
| 5,022,416 A | 6/1991 | Watson |
| 5,042,510 A | 8/1991 | Curtiss et al. |
| 5,056,537 A | 10/1991 | Brown et al. |
| 5,060,669 A | 10/1991 | White et al. |
| 5,060,671 A | 10/1991 | Counts et al. |
| 5,065,775 A | 11/1991 | Fagg |
| 5,072,744 A | 12/1991 | Luke et al. |
| 5,074,319 A | 12/1991 | White et al. |
| 5,076,296 A | 12/1991 | Nystrom et al. |
| 5,093,894 A | 3/1992 | Deevi et al. |
| 5,095,921 A | 3/1992 | Losee et al. |
| 5,097,850 A | 3/1992 | Braunshteyn et al. |
| 5,099,862 A | 3/1992 | White et al. |
| 5,099,864 A | 3/1992 | Young et al. |
| 5,103,842 A | 4/1992 | Strang et al. |
| 5,121,757 A | 6/1992 | White et al. |
| 5,129,409 A | 7/1992 | White et al. |
| 5,131,415 A | 7/1992 | Munoz et al. |
| 5,143,097 A | 9/1992 | Stephen Sohn et al. |
| 5,144,962 A | 9/1992 | Counts et al. |
| 5,146,934 A | 9/1992 | Deevi et al. |
| 5,159,940 A | 11/1992 | Hayward et al. |
| 5,159,942 A | 11/1992 | Brinkley et al. |
| 5,179,966 A | 1/1993 | Losee et al. |
| 5,211,684 A | 5/1993 | Shannon et al. |
| 5,220,930 A | 6/1993 | Gentry |
| 5,224,498 A | 7/1993 | Deevi et al. |
| 5,228,460 A | 7/1993 | Sprinkel et al. |
| 5,230,354 A | 7/1993 | Smith et al. |
| 5,235,992 A | 8/1993 | Sensabaugh, Jr. |
| 5,243,999 A | 9/1993 | Smith |
| 5,246,018 A | 9/1993 | Deevi et al. |
| 5,249,586 A | 10/1993 | Morgan et al. |
| 5,261,424 A | 11/1993 | Sprinkel, Jr. |
| 5,269,327 A | 12/1993 | Counts et al. |
| 5,285,798 A | 2/1994 | Banerjee et al. |
| 5,293,883 A | 3/1994 | Edwards |
| 5,301,694 A | 4/1994 | Raymond et al. |
| 5,303,720 A | 4/1994 | Banerjee et al. |
| 5,318,050 A | 6/1994 | Gonzalez-Parra et al. |
| 5,322,075 A | 6/1994 | Deevi et al. |
| 5,322,076 A | 6/1994 | Brinkley et al. |
| 5,339,838 A | 8/1994 | Young et al. |
| 5,345,951 A | 9/1994 | Serrano et al. |
| 5,353,813 A | 10/1994 | Deevi et al. |
| 5,357,984 A | 10/1994 | Farrier et al. |
| 5,360,023 A | 11/1994 | Blakley et al. |
| 5,369,723 A | 11/1994 | Counts et al. |
| 5,372,148 A | 12/1994 | McCafferty et al. |
| 5,377,698 A | 1/1995 | Litzinger et al. |
| 5,388,574 A | 2/1995 | Ingebrethsen |
| 5,388,594 A | 2/1995 | Counts et al. |
| 5,408,574 A | 4/1995 | Deevi et al. |
| 5,435,325 A | 7/1995 | Clapp et al. |
| 5,445,169 A | 8/1995 | Brinkley et al. |
| 5,468,266 A | 11/1995 | Bensalem et al. |
| 5,468,936 A | 11/1995 | Deevi et al. |
| 5,479,948 A | 1/1996 | Counts et al. |
| 5,498,850 A | 3/1996 | Das |
| 5,498,855 A | 3/1996 | Deevi et al. |
| 5,499,636 A | 3/1996 | Baggett, Jr. et al. |
| 5,501,237 A | 3/1996 | Young et al. |
| 5,505,214 A | 4/1996 | Collins et al. |
| 5,515,842 A | 5/1996 | Ramseyer et al. |
| 5,530,225 A | 6/1996 | Hajaligol |
| 5,551,450 A | 9/1996 | Hemsley |
| 5,551,451 A | 9/1996 | Riggs et al. |
| 5,564,442 A | 10/1996 | MacDonald et al. |
| 5,573,692 A | 11/1996 | Das et al. |

(56) References Cited

U.S. PATENT DOCUMENTS

| | | |
|---|---|---|
| 5,591,368 A | 1/1997 | Fleischhauer et al. |
| 5,593,792 A | 1/1997 | Farrier et al. |
| 5,595,577 A | 1/1997 | Bensalem et al. |
| 5,596,706 A | 1/1997 | Shimazaki et al. |
| 5,611,360 A | 3/1997 | Tang |
| 5,613,504 A | 3/1997 | Collins et al. |
| 5,613,505 A | 3/1997 | Campbell et al. |
| 5,649,552 A | 7/1997 | Cho et al. |
| 5,649,554 A | 7/1997 | Sprinkel et al. |
| 5,659,656 A | 8/1997 | Das |
| 5,665,262 A | 9/1997 | Hajaligol et al. |
| 5,666,976 A | 9/1997 | Adams et al. |
| 5,666,977 A | 9/1997 | Higgins et al. |
| 5,666,978 A | 9/1997 | Counts et al. |
| 5,687,746 A | 11/1997 | Rose et al. |
| 5,692,525 A | 12/1997 | Counts et al. |
| 5,692,526 A | 12/1997 | Adams et al. |
| 5,708,258 A | 1/1998 | Counts et al. |
| 5,711,320 A | 1/1998 | Martin |
| 5,726,421 A | 3/1998 | Fleischhauer et al. |
| 5,727,571 A | 3/1998 | Meiring et al. |
| 5,730,158 A | 3/1998 | Collins et al. |
| 5,750,964 A | 5/1998 | Counts et al. |
| 5,799,663 A | 9/1998 | Gross et al. |
| 5,816,263 A | 10/1998 | Counts et al. |
| 5,819,756 A | 10/1998 | Mielordt |
| 5,829,453 A | 11/1998 | White et al. |
| 5,865,185 A | 2/1999 | Collins et al. |
| 5,865,186 A | 2/1999 | Volsey, II |
| 5,878,752 A | 3/1999 | Adams et al. |
| 5,880,439 A | 3/1999 | Deevi et al. |
| 5,894,841 A | 4/1999 | Voges |
| 5,915,387 A | 6/1999 | Baggett, Jr. et al. |
| 5,934,289 A | 8/1999 | Watkins et al. |
| 5,954,979 A | 9/1999 | Counts et al. |
| 5,967,148 A | 10/1999 | Harris et al. |
| 6,026,820 A | 2/2000 | Baggett, Jr. et al. |
| 6,033,623 A | 3/2000 | Deevi et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,116,247 A | 9/2000 | Banyasz et al. |
| 6,119,700 A | 9/2000 | Fleischhauer et al. |
| 6,125,853 A | 10/2000 | Susa et al. |
| 6,125,855 A | 10/2000 | Nevett et al. |
| 6,125,866 A | 10/2000 | Nichols et al. |
| 6,155,268 A | 12/2000 | Takeuchi |
| 6,164,287 A | 12/2000 | White |
| 6,182,670 B1 | 2/2001 | White et al. |
| 6,196,218 B1 | 3/2001 | Voges |
| 6,196,219 B1 | 3/2001 | Hess et al. |
| 6,216,706 B1 | 4/2001 | Kumar et al. |
| 6,289,898 B1 | 9/2001 | Fournier et al. |
| 6,349,729 B1 | 2/2002 | Meyer et al. |
| 6,357,671 B1 | 3/2002 | Cewers |
| 6,418,938 B1 | 7/2002 | Fleischhauer et al. |
| 6,446,426 B1 | 9/2002 | Sweeney et al. |
| 6,532,965 B1 | 3/2003 | Abhulimen et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,701,936 B2 | 3/2004 | Shafer et al. |
| 6,715,494 B1 | 4/2004 | McCoy |
| 6,730,832 B1 | 5/2004 | Dominguez et al. |
| 6,772,756 B2 | 8/2004 | Shayan |
| 6,803,545 B2 | 10/2004 | Blake et al. |
| 6,803,550 B2 | 10/2004 | Sharpe et al. |
| 6,810,883 B2 | 11/2004 | Felter et al. |
| 6,854,461 B2 | 2/2005 | Nichols et al. |
| 6,854,470 B1 | 2/2005 | Pu |
| 6,994,096 B2 | 2/2006 | Rostami et al. |
| 7,011,096 B2 | 3/2006 | Li et al. |
| 7,017,585 B2 | 3/2006 | Li et al. |
| 7,025,066 B2 | 4/2006 | Lawson et al. |
| 7,117,867 B2 | 10/2006 | Cox et al. |
| 7,163,015 B2 | 1/2007 | Moffitt |
| 7,173,322 B2 | 2/2007 | Sakata et al. |
| 7,185,659 B2 | 3/2007 | Sharpe |
| 7,234,470 B2 | 6/2007 | Yang |
| 7,290,549 B2 | 11/2007 | Banerjee et al. |
| 7,293,565 B2 | 11/2007 | Griffin et al. |
| 7,392,809 B2 | 7/2008 | Larson et al. |
| 7,513,253 B2 | 4/2009 | Kobayashi et al. |
| 7,647,932 B2 | 1/2010 | Cantrell et al. |
| 7,690,385 B2 | 4/2010 | Moffitt |
| 7,692,123 B2 | 4/2010 | Baba et al. |
| 7,726,320 B2 | 6/2010 | Robinson et al. |
| 7,775,459 B2 | 8/2010 | Martens, III et al. |
| 7,810,505 B2 | 10/2010 | Yang |
| 7,832,410 B2 | 11/2010 | Hon |
| 7,845,359 B2 | 12/2010 | Montaser |
| 7,878,209 B2 | 2/2011 | Newbery et al. |
| 7,896,006 B2 | 3/2011 | Hamano et al. |
| 8,066,010 B2 | 11/2011 | Newbery et al. |
| 8,079,371 B2 | 12/2011 | Robinson et al. |
| 8,127,772 B2 | 3/2012 | Montaser |
| 8,156,944 B2 | 4/2012 | Han |
| 8,314,591 B2 | 11/2012 | Terry et al. |
| 8,365,742 B2 | 2/2013 | Hon |
| 8,375,957 B2 | 2/2013 | Hon |
| 8,393,331 B2 | 3/2013 | Hon |
| 8,402,976 B2 | 3/2013 | Fernando et al. |
| 8,499,766 B1 | 8/2013 | Newton |
| 8,528,569 B1 | 9/2013 | Newton |
| 8,550,069 B2 | 10/2013 | Alelov |
| 8,851,081 B2 | 10/2014 | Fernando et al. |
| 2002/0146242 A1 | 10/2002 | Vieira |
| 2003/0131859 A1 | 7/2003 | Li et al. |
| 2003/0226837 A1 | 12/2003 | Blake et al. |
| 2004/0020500 A1 | 2/2004 | Wrenn et al. |
| 2004/0118401 A1 | 6/2004 | Smith et al. |
| 2004/0129280 A1 | 7/2004 | Woodson et al. |
| 2004/0149296 A1 | 8/2004 | Rostami et al. |
| 2004/0200488 A1 | 10/2004 | Felter et al. |
| 2004/0226568 A1 | 11/2004 | Takeuchi et al. |
| 2004/0255965 A1 | 12/2004 | Perfetti et al. |
| 2005/0016549 A1 | 1/2005 | Banerjee et al. |
| 2005/0016550 A1 | 1/2005 | Katase |
| 2005/0066986 A1 | 3/2005 | Nestor et al. |
| 2005/0172976 A1 | 8/2005 | Newman et al. |
| 2005/0274390 A1 | 12/2005 | Banerjee et al. |
| 2006/0016453 A1 | 1/2006 | Kim |
| 2006/0070633 A1 | 4/2006 | Rostami et al. |
| 2006/0130860 A1 | 6/2006 | Cholet |
| 2006/0162733 A1 | 7/2006 | McGrath et al. |
| 2006/0185687 A1 | 8/2006 | Hearn et al. |
| 2006/0196518 A1 | 9/2006 | Hon |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2007/0283972 A1 | 12/2007 | Monsees et al. |
| 2008/0085103 A1 | 4/2008 | Beland et al. |
| 2008/0092912 A1 | 4/2008 | Robinson et al. |
| 2008/0149118 A1 | 6/2008 | Oglesby et al. |
| 2008/0245377 A1 | 10/2008 | Marshall et al. |
| 2008/0257367 A1 | 10/2008 | Paterno et al. |
| 2008/0262469 A1 | 10/2008 | Brister et al. |
| 2008/0276947 A1 | 11/2008 | Martzel |
| 2008/0302374 A1 | 12/2008 | Wengert et al. |
| 2009/0065010 A1 | 3/2009 | Shands |
| 2009/0095311 A1 | 4/2009 | Han |
| 2009/0095312 A1 | 4/2009 | Herbrich et al. |
| 2009/0126745 A1 | 5/2009 | Hon |
| 2009/0188490 A1 | 7/2009 | Han |
| 2009/0230117 A1 | 9/2009 | Fernando et al. |
| 2009/0260641 A1 | 10/2009 | Monsees et al. |
| 2009/0260642 A1 | 10/2009 | Monsees et al. |
| 2009/0272379 A1 | 11/2009 | Thorens et al. |
| 2009/0283103 A1* | 11/2009 | Nielsen .......... A24F 40/40 131/273 |
| 2009/0293892 A1 | 12/2009 | Williams et al. |
| 2009/0320863 A1 | 12/2009 | Fernando et al. |

(56) References Cited

U.S. PATENT DOCUMENTS

| | | |
|---|---|---|
| 2009/0324206 A1 | 12/2009 | Young et al. |
| 2010/0006113 A1 | 1/2010 | Urtsev et al. |
| 2010/0024834 A1 | 2/2010 | Oglesby et al. |
| 2010/0043809 A1 | 2/2010 | Magnon |
| 2010/0059070 A1 | 3/2010 | Potter et al. |
| 2010/0059073 A1 | 3/2010 | Hoffmann et al. |
| 2010/0065075 A1 | 3/2010 | Banerjee et al. |
| 2010/0083959 A1 | 4/2010 | Siller |
| 2010/0163063 A1 | 7/2010 | Fernando et al. |
| 2010/0200006 A1 | 8/2010 | Robinson et al. |
| 2010/0229881 A1 | 9/2010 | Hearn |
| 2010/0242974 A1 | 9/2010 | Pan |
| 2010/0242976 A1 | 9/2010 | Katayama et al. |
| 2010/0252036 A1* | 10/2010 | Sutherland ............. G16H 20/10 709/201 |
| 2010/0258139 A1 | 10/2010 | Onishi et al. |
| 2010/0300467 A1 | 12/2010 | Kuistila et al. |
| 2010/0307518 A1 | 12/2010 | Wang |
| 2010/0313901 A1 | 12/2010 | Fernando et al. |
| 2011/0005535 A1 | 1/2011 | Xin |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0073121 A1 | 3/2011 | Levin et al. |
| 2011/0088707 A1 | 4/2011 | Hajaligol |
| 2011/0094523 A1 | 4/2011 | Thorens et al. |
| 2011/0120480 A1 | 5/2011 | Gedevanishvili et al. |
| 2011/0126847 A1 | 6/2011 | El-Shall et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0162663 A1 | 7/2011 | Bryman |
| 2011/0168194 A1 | 7/2011 | Hon |
| 2011/0180082 A1 | 7/2011 | Banerjee et al. |
| 2011/0265806 A1* | 11/2011 | Alarcon ................. A24F 40/50 131/273 |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0037041 A1 | 2/2013 | Worm et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0192619 A1 | 8/2013 | Tucker et al. |
| 2013/0284192 A1* | 10/2013 | Peleg ...................... A24F 40/65 131/329 |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0014125 A1 | 1/2014 | Fernando et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2015/0007838 A1 | 1/2015 | Fernando et al. |

FOREIGN PATENT DOCUMENTS

| | | |
|---|---|---|
| CA | 2 752 255 | 8/2010 |
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| DE | 10 2006 004 484 | 8/2007 |
| DE | 10 2006 041 042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 1989946 | 11/2008 |
| EP | 2110034 | 10/2009 |
| EP | 2 316 286 | 5/2011 |
| EP | 2 454 956 | 5/2012 |
| EP | 2 468 116 | 6/2012 |
| GB | 1444461 | 7/1976 |
| GB | 2469850 | 11/2010 |
| JP | 2004-180440 A | 6/2004 |
| JP | 2011-141861 A | 7/2011 |
| JP | 2012-27245 A | 2/2012 |
| JP | 2012078916 | 4/2012 |
| JP | 2012527222 | 11/2012 |
| JP | 2013054733 | 3/2013 |
| JP | 2013120418 | 6/2013 |
| JP | 2013524835 | 6/2013 |
| JP | 2013219666 | 10/2013 |
| WO | WO 0237990 | 5/2002 |
| WO | WO 198602528 | 5/2002 |
| WO | WO 199748293 | 5/2002 |
| WO | WO 2004043175 | 5/2004 |
| WO | WO 2005099494 | 10/2005 |
| WO | WO 2007078273 | 7/2007 |
| WO | WO 2007131449 | 11/2007 |
| WO | WO 2009105919 | 9/2009 |
| WO | WO 2009155734 | 12/2009 |
| WO | WO 2010003480 | 1/2010 |
| WO | WO 2010045670 | 4/2010 |
| WO | WO 2010073122 | 7/2010 |
| WO | WO 2010091593 | 8/2010 |
| WO | WO 2010118644 | 10/2010 |
| WO | WO 2010140937 | 12/2010 |
| WO | WO 2011010334 | 1/2011 |
| WO | WO 2011081558 | 7/2011 |
| WO | WO 2012065754 | 5/2012 |
| WO | WO 2012072762 | 6/2012 |
| WO | WO 2012100523 | 8/2012 |
| WO | WO 2013089551 | 6/2013 |
| WO | WO 2013093695 | 6/2013 |

OTHER PUBLICATIONS

Meet Smokio—The First Connected Electronic Cigarette website visited Jan. 21, 2014 www.smokio.com.

International Search Report and Written Opinion for International Application No. PCT/US2015/014574 dated Apr. 28, 2015.

* cited by examiner

RECEIVING A SOFTWARE UPDATE FROM THE COMPUTING DEVICE
1000

USING THE SOFTWARE UPDATE TO UPDATE A SOFTWARE
CONFIGURATION OF THE AEROSOL DELIVERY DEVICE
1010

*FIG. 10*

CHARGING ACCESSORY DEVICE FOR AN AEROSOL DELIVERY DEVICE AND RELATED SYSTEM, METHOD, APPARATUS, AND COMPUTER PROGRAM PRODUCT FOR PROVIDING INTERACTIVE SERVICES FOR AEROSOL DELIVERY DEVICES

CROSS-REFERENCE TO RELATED APPLICATION(S)

The present application is a continuation of U.S. patent application Ser. No. 14/175,391, filed Feb. 7, 2014, entitled: Charging Accessory Device for an Aerosol Delivery Device and Related System, Method, Apparatus, and Computer Program Product for Providing Interactive Services for Aerosol Delivery Devices, the content of which is incorporated herein by reference in its entirety.

FIELD OF THE DISCLOSURE

The present disclosure relates to aerosol delivery devices such as smoking articles, and more particularly to a charging accessory device for the aerosol delivery device and related systems, methods, apparatuses, and computer program products for providing interactive services for aerosol delivery devices. The smoking articles may be configured to heat a material, which may be made or derived from tobacco or otherwise incorporate tobacco, to form an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al., U.S. Pat. U.S. App. Pub. No. 2013/0255702 to Griffith, Jr. et al., U.S. patent application Ser. No. 13/536,438 U.S. Pat. App. Pub. No. 2014/0000638 to Sebastian et al., U.S. patent application Ser. No. 13/602,871, filed Sep. 4, 2012, and U.S. patent application Ser. No. 13/647,000, filed Oct. 8, 2012, which are incorporated herein by reference.

While aerosol delivery devices continue to increase in popularity and sophistication, there continues to be a lack of interactive services available for aerosol delivery devices. Accordingly, it would be desirable to provide aerosol delivery devices and users thereof with interactive services that enhance the social aspects of using aerosol delivery devices.

SUMMARY OF THE DISCLOSURE

The present disclosure relates to a charging accessory device and related systems, methods, apparatuses, and computer program products for providing interactive services for aerosol delivery devices. For example, in one aspect, a charging accessory device is provided. The charging accessory device may include a housing defining a receptacle configured to receive at least a portion of an aerosol delivery device comprising a battery. The charging accessory device may further include a power storage device and a charging interface configured to establish an electrical connection with the battery and to supply electrical power from the power storage device to the battery to charge the battery. The charging accessory device may also include an aerosol delivery device interface, which may be configured to enable communication between the charging accessory device and a control component of the aerosol delivery device. The charging accessory device may additionally include a communication interface. The charging accessory device may further include processing circuitry, which may be configured to control the charging accessory device to at least access usage data for the aerosol delivery device via the aerosol delivery device interface; and cause, via the communication interface, social data derived based at least in part on the usage data to be provided to a social networking service comprising a community of aerosol delivery device users.

In another aspect, a system for providing interactive services for aerosol delivery devices is provided. The system may include at least a portion of an aerosol delivery device, which may include a control component configured to maintain usage data for the aerosol delivery device; and a battery. The system may additionally include a computing device, which may be configured to access a network to communicate with a social networking service comprising a community of aerosol delivery device users. The system may further include a charging accessory device including a housing defining a receptacle configured to receive the at least a portion of the aerosol delivery device and a power storage device. The charging accessory device may be configured to supply power from the power storage device to charge the battery of the aerosol delivery device and to communicate with the control component to access the usage data. The charging accessory device may further include a communication interface, which may be configured to enable communication between the charging accessory device and the computing device. The computing device may be further configured to receive the usage data from the charging accessory device; generate social data based at least in part on the usage data; and send the social data to the social networking service.

In a further aspect, a method for providing interactive services for aerosol delivery devices is provided. The method may include a computing device establishing communication with a charging accessory device for an aerosol delivery device. The method may further include the computing device receiving usage data for the aerosol delivery device provided by the charging accessory device. The method may additionally include the computing device generating social data based at least in part on the usage data; and sending the social data to a social networking service comprising a community of aerosol delivery device users.

In an additional aspect, a computing device comprising processing circuitry is provided. The processing circuitry may be configured to cause the computing device to establish communication with a charging accessory device for an aerosol delivery device. The processing circuitry may be further configured to cause the computing device to receive usage data for the aerosol delivery device provided by the charging accessory device. The processing circuitry may additionally be configured to cause the computing device to generate social data based at least in part on the usage data; and to send the social data to a social networking service comprising a community of aerosol delivery device users.

In a further aspect, a computer program product is provided, which may include at least one non-transitory computer-readable storage medium having program instructions stored thereon. When executed by at least one processor, the stored program instructions may cause the at least one processor to perform a method comprising establishing communication with a charging accessory device for an aerosol delivery device; receiving usage data for the aerosol delivery device provided by the charging accessory device; generating social data based at least in part on the usage data; and sending the social data to a social networking service comprising a community of aerosol delivery device users.

BRIEF DESCRIPTION OF THE FIGURES

Figure 1:
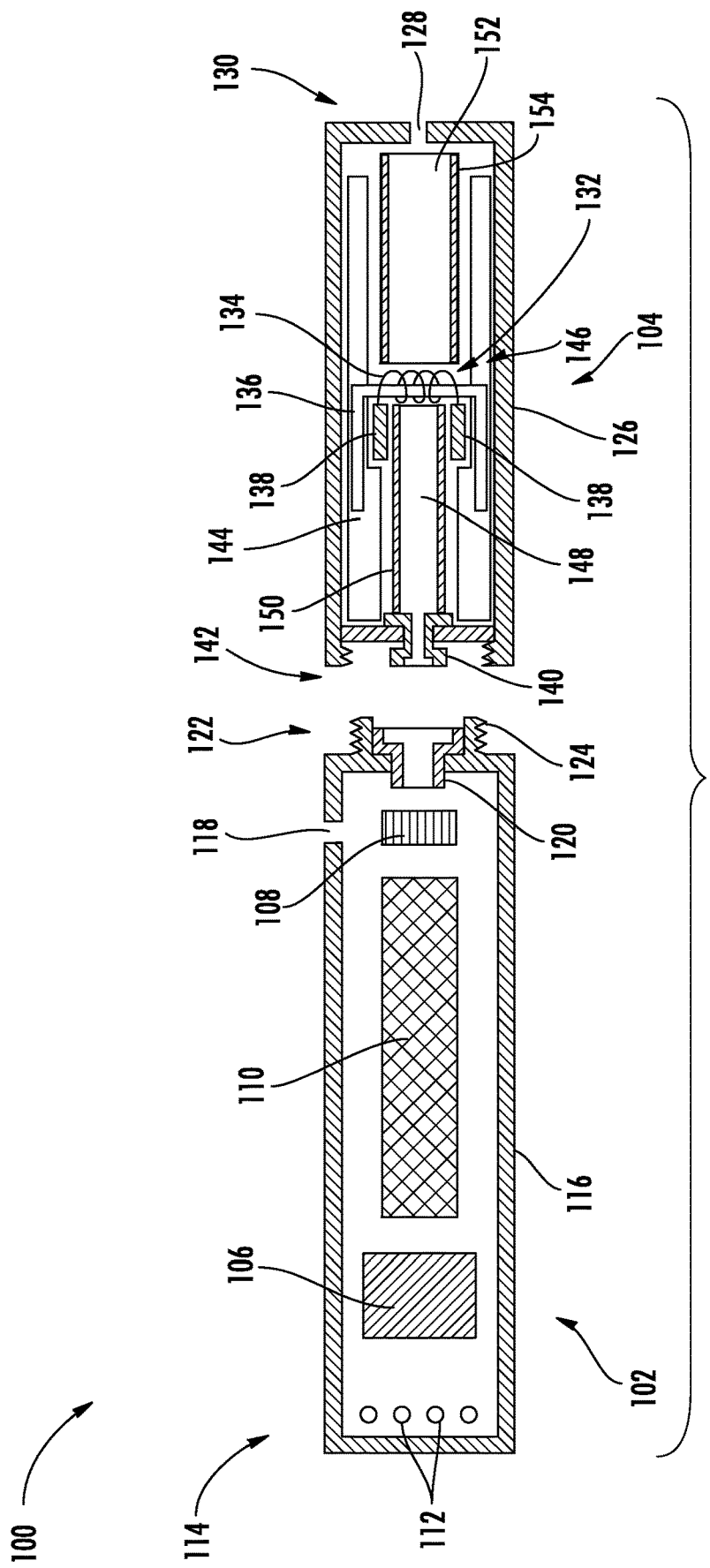
Figure 2:
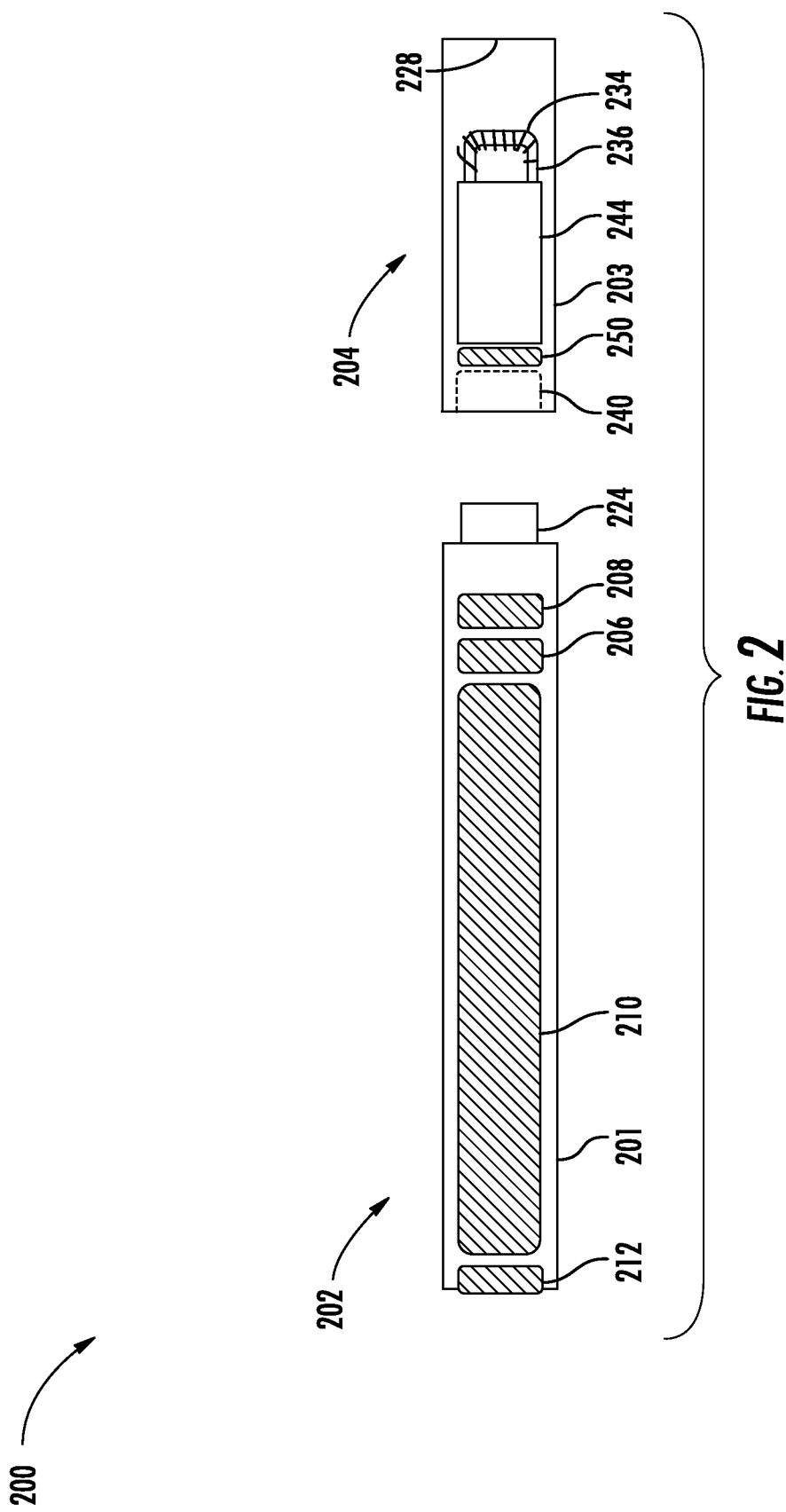
Figure 3:
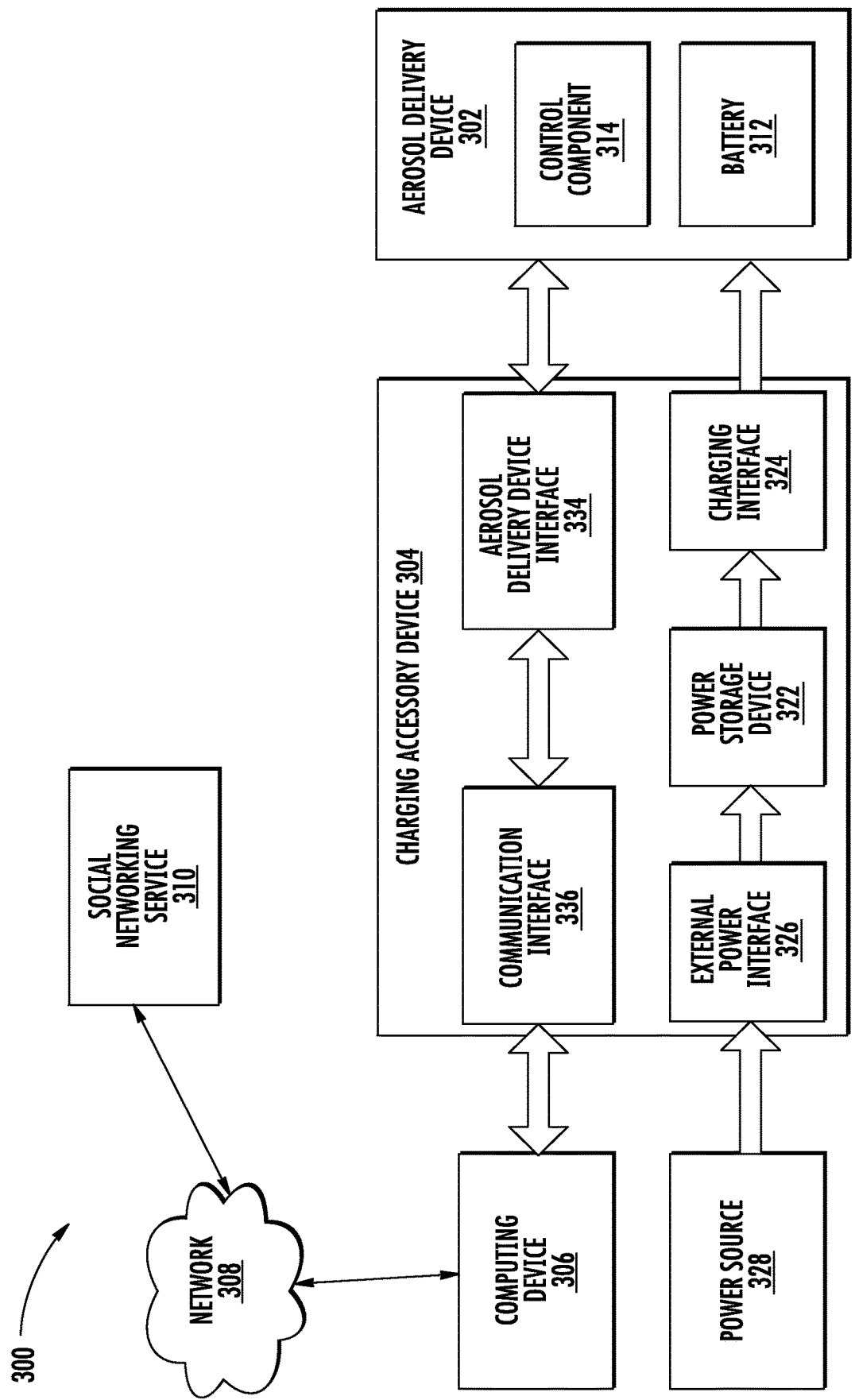
Figure 4:
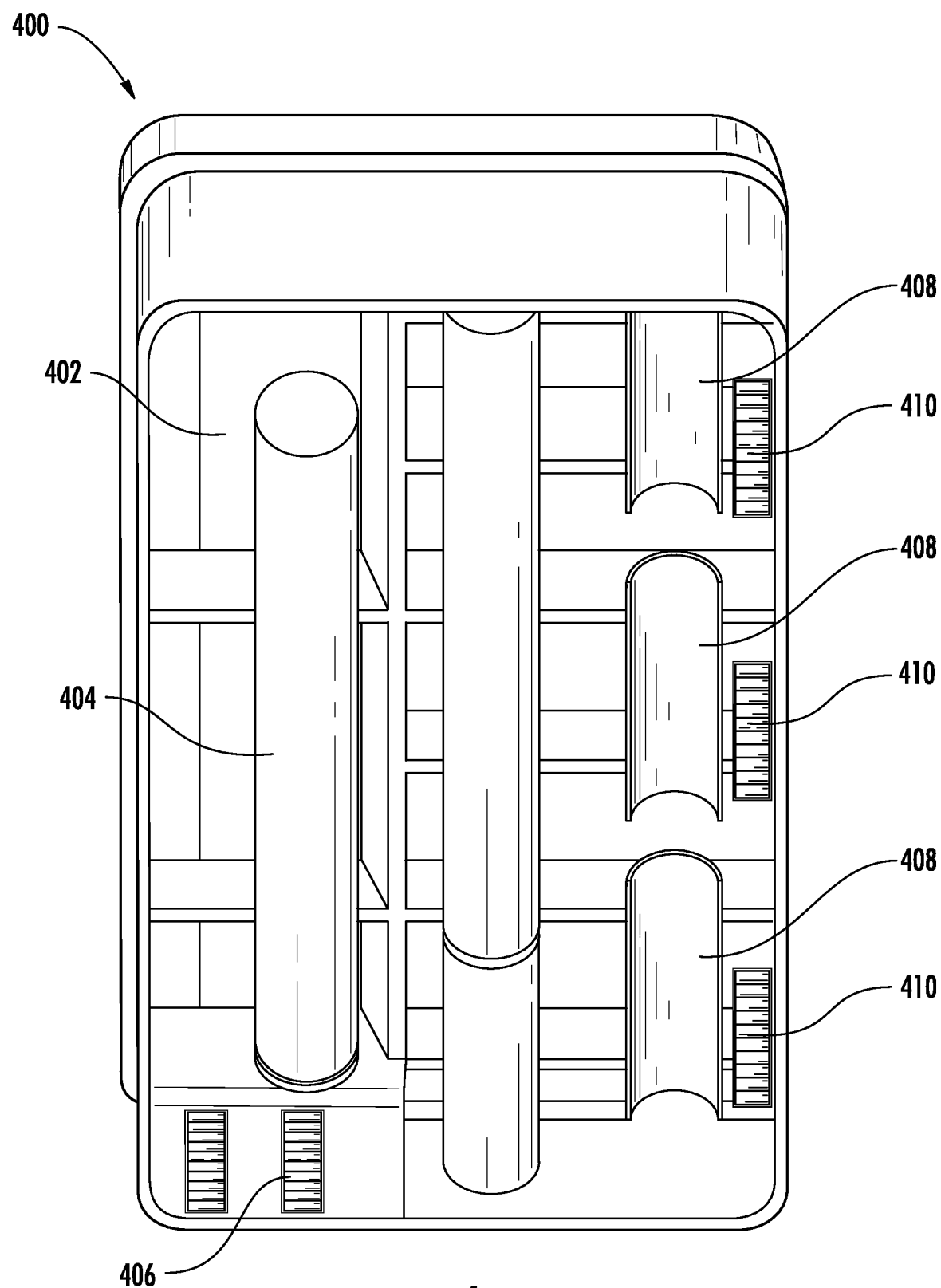
Figure 5:
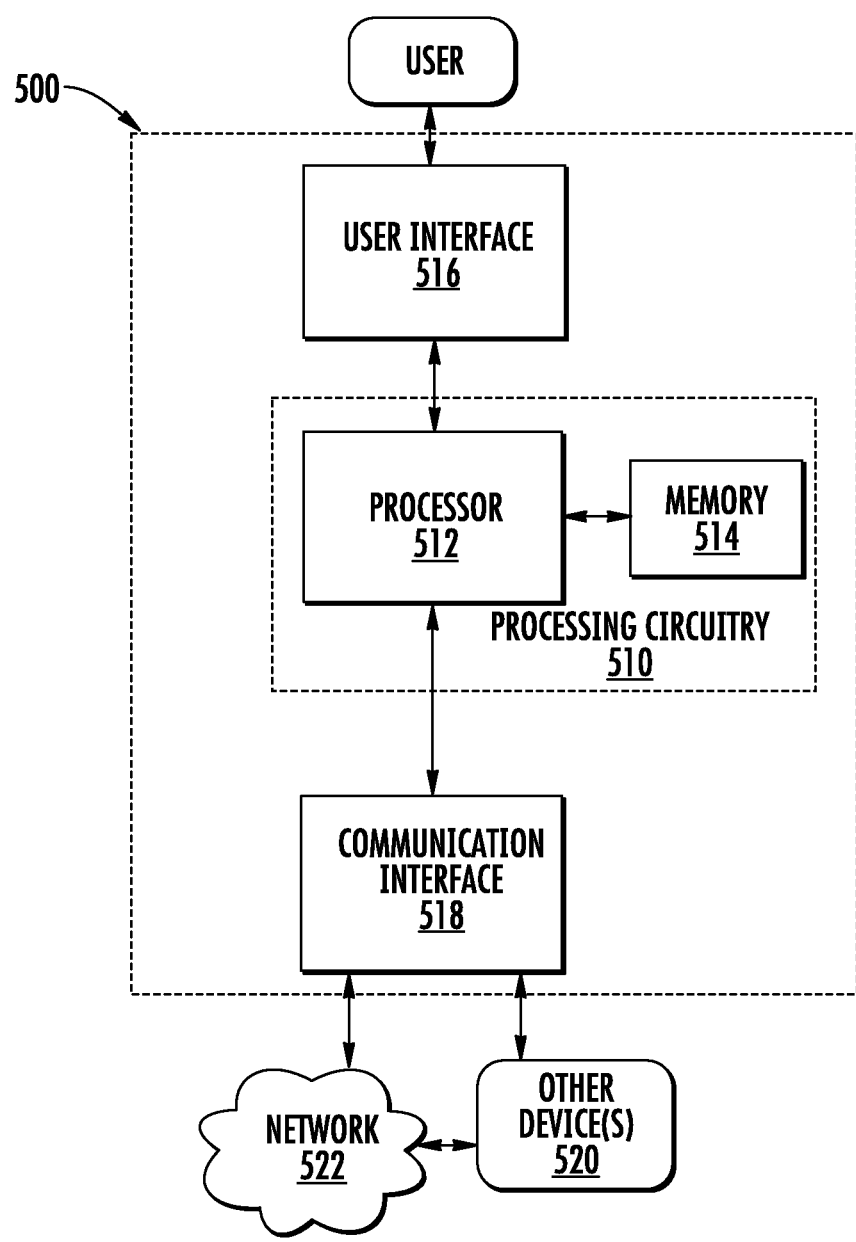
Figure 6:
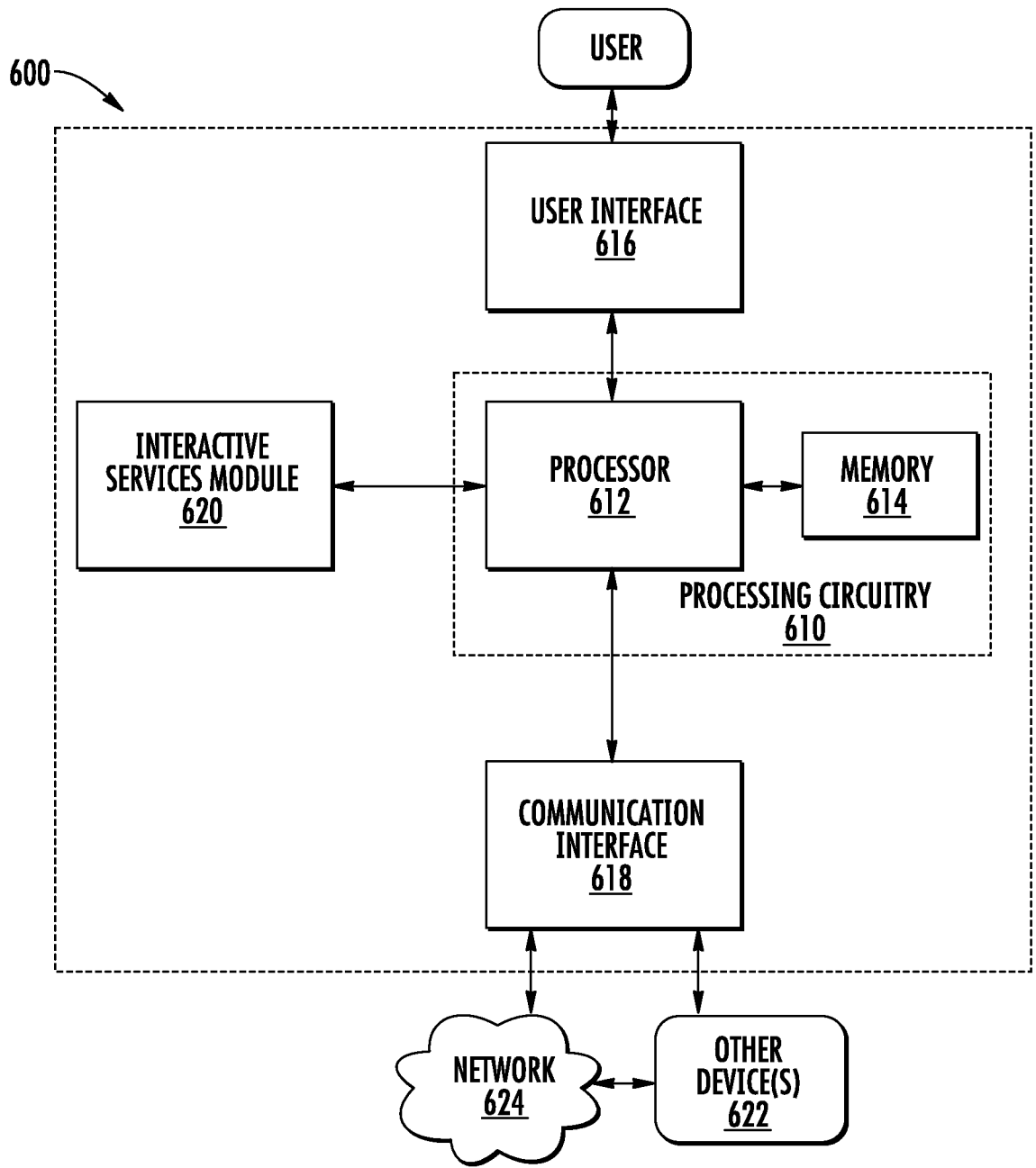
Figure 7:
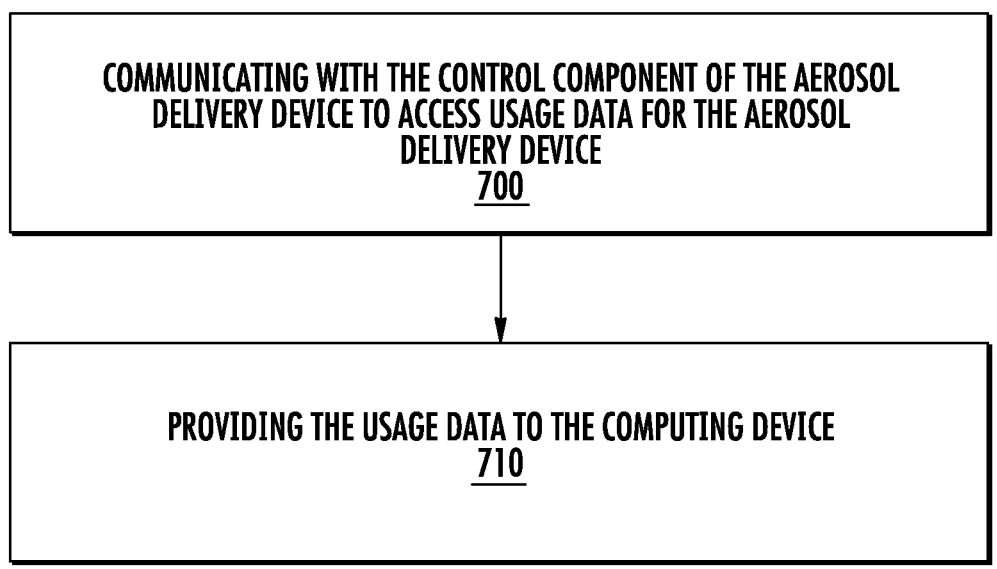
Figure 8:
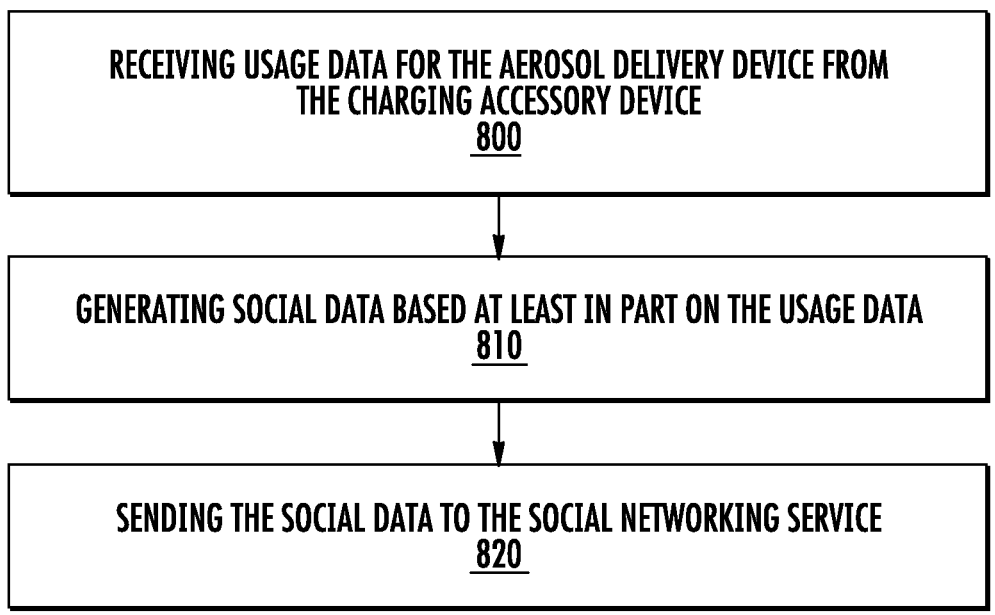
Figure 9:
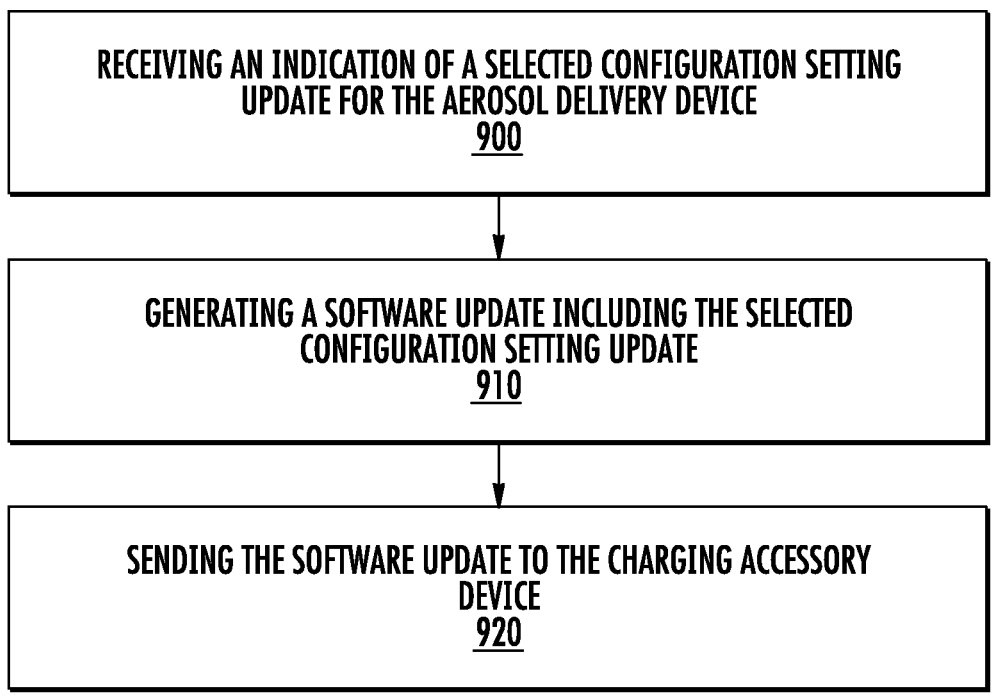

Having thus described the disclosure in the foregoing general terms, reference will now be made to the accompanying drawings, which are not necessarily drawn to scale, and wherein:

FIG. 1 is a sectional view through an electronic smoking article comprising a control body and a cartridge according to an example embodiment of the present disclosure;

FIG. 2 is a sectional view through an electronic smoking article comprising a cartridge and a control body and including a reservoir housing according to an example embodiment of the present disclosure;

FIG. 3 illustrates a system including a charging accessory device for providing interactive services for aerosol delivery devices in accordance with some example embodiments of the present disclosure;

FIG. 4 illustrates an example housing of a charging accessory device in accordance with some example embodiments of the present disclosure;

FIG. 5 illustrates a block diagram of an apparatus that may be implemented on a charging accessory device in accordance with some example embodiments of the present disclosure;

FIG. 6 illustrates a block diagram of an apparatus that may be implemented on a computing device configured to provide interactive services for an aerosol delivery device in accordance with some example embodiments of the present disclosure;

FIG. 7 illustrates a flowchart according to an example method that may be performed by a charging accessory device to collect and provide access to usage data for an aerosol delivery device to a computing device for use in providing interactive services in accordance with some example embodiments of the present disclosure;

FIG. 8 illustrates a flowchart according to an example method for providing social data generated based at least in part on aerosol delivery device usage data provided by a charging accessory device to a social networking service in accordance with some example embodiments of the present disclosure;

FIG. 9 illustrates a flowchart according to an example method for providing a software update for an aerosol delivery device to a charging accessory device in accordance with some example embodiments of the present disclosure; and FIG. 10 illustrates a flowchart according to an example method that may be performed by a charging accessory device to update a software configuration of an aerosol delivery device in accordance with some example embodiments of the present disclosure.

DETAILED DESCRIPTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

Some example embodiments of the present disclosure relate to a charging accessory device for the aerosol delivery device and related systems, methods, apparatuses, and computer program products for providing interactive services for aerosol delivery devices. Aerosol delivery devices (e.g., smoking articles) that may be used with various example embodiments may, by way of non-limiting example, include so-called "e-cigarettes." It should be understood that the mechanisms, components, features, and methods associated with such aerosol delivery devices may be embodied in many different forms and associated with a variety of articles.

In this regard, the present disclosure provides descriptions of aerosol delivery devices that use electrical energy to heat a material (preferably without combusting the material to any significant degree) to form an inhalable substance; such articles most preferably being sufficiently compact to be considered "hand-held" devices. An aerosol delivery device may provide some or all of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe, without any substantial degree of combustion of any component of that article or device. The aerosol delivery device may not produce smoke in the sense of the aerosol resulting from by-products of combustion or pyrolysis of tobacco, but rather, that the article or device may yield vapors (including vapors within aerosols that can be considered to be visible aerosols that might be considered to be described as smoke-like) resulting from volatilization or vaporization of certain components of the article or device. In highly preferred embodiments, aerosol delivery devices may incorporate tobacco and/or components derived from tobacco.

Aerosol delivery devices of the present disclosure also can be characterized as being vapor-producing articles, smoking articles, or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

Aerosol delivery devices of the present disclosure generally include a number of components provided within an outer body or shell. The overall design of the outer body or shell can vary, and the format or configuration of the outer body that can define the overall size and shape of the aerosol delivery device can vary. Typically, an elongated body resembling the shape of a cigarette or cigar can be a formed from a single, unitary shell; or the elongated body can be formed of two or more separable pieces. For example, an aerosol delivery device can comprise an elongated shell or body that can be substantially tubular in shape and, as such, resemble the shape of a conventional cigarette or cigar. In one embodiment, all of the components of the aerosol delivery device are contained within one outer body or shell. Alternatively, an aerosol delivery device can comprise two or more shells that are joined and are separable. For example, an aerosol delivery device can possess at one end a control body comprising an outer body or shell containing one or more reusable components (e.g., a rechargeable battery and various electronics for controlling the operation of that article), and at the other end and removably attached thereto an outer body or shell containing a disposable portion (e.g., a disposable flavor-containing cartridge). More specific formats, configurations and arrangements of components within the single shell type of unit or within a multi-piece separable shell type of unit will be evident in light of the further disclosure provided herein.

Additionally, various aerosol delivery device designs and component arrangements can be appreciated upon consideration of the commercially available electronic aerosol delivery devices, such as those representative products listed in the background art section of the present disclosure.

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microcontroller), a heater or heat generation component (e.g., an electrical resistance heating element or component commonly referred to as an "atomizer"), and an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined air flow path through the article such that aerosol generated can be withdrawn therefrom upon draw). Exemplary formulations for aerosol precursor materials that may be used according to the present disclosure are described in U.S. Pat. Pub. No. 2013/0008457 to Zheng et al., the disclosure of which is incorporated herein by reference in its entirety.

Alignment of the components within the aerosol delivery device can vary. In specific embodiments, the aerosol precursor composition can be located near an end of the article (e.g., within a cartridge, which in certain circumstances can be replaceable and disposable), which may be proximal to the mouth of a user so as to maximize aerosol delivery to the user. Other configurations, however, are not excluded. Generally, the heating element can be positioned sufficiently near the aerosol precursor composition so that heat from the heating element can volatilize the aerosol precursor (as well as one or more flavorants, medicaments, or the like that may likewise be provided for delivery to a user) and form an aerosol for delivery to the user.

When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof. Additionally, the selection of various aerosol delivery device components can be appreciated upon consideration of the commercially available electronic aerosol delivery devices, such as those representative products listed in the background art section of the present disclosure.

An aerosol delivery device incorporates a battery or other electrical power source to provide current flow sufficient to provide various functionalities to the article, such as resistive heating, powering of control systems, powering of indicators, and the like. The power source can take on various embodiments. Preferably, the power source is able to deliver sufficient power to rapidly heat the heating member to provide for aerosol formation and power the article through use for the desired duration of time. The power source preferably is sized to fit conveniently within the aerosol delivery device so that the aerosol delivery device can be easily handled; and additionally, a preferred power source is of a sufficiently light weight to not detract from a desirable smoking experience.

One example embodiment of an aerosol delivery device 100 that may be used with various embodiments is provided in FIG. 1. As seen in the cross-section illustrated therein, the aerosol delivery device 100 can comprise a control body 102 and a cartridge 104 that can be permanently or detachably aligned in a functioning relationship. Although a threaded engagement is illustrated in FIG. 1, it is understood that further means of engagement may be employed, such as a press-fit engagement, interference fit, a magnetic engagement, or the like. In specific embodiments, one or both of the control body 102 and the cartridge 104 may be referred to as being disposable or as being reusable. For example, the control body may have a replaceable battery or a rechargeable battery and thus may be combined with any type of recharging technology, including connection to a typical electrical outlet, connection to a car charger (e.g., cigarette lighter receptacle), and connection to a computer, such as through a universal serial bus (USB) cable. For example, an adaptor including a USB connector at one end and a control body connector at an opposing end is disclosed in U.S. patent application Ser. No. 13/840,264, filed Mar. 15, 2013, which is incorporated herein by reference in its entirety. As a further example, in some embodiments, the battery may be recharged through interfacing of the aerosol delivery device 100 or portion thereof containing a battery (e.g., the control body 102) with an embodiment of the charging accessory device discussed further herein below. It will be appreciated that embodiments including a rechargeable battery may include any type of rechargeable battery, such as by way of non-limiting example, a lithium ion battery (e.g., a rechargeable lithium-manganese dioxide battery), lithium ion polymer battery, nickel-zinc battery, nickel-metal hydride battery, nickel cadmium battery, rechargeable alkaline battery, some combination thereof, and/or other type of rechargeable battery. Further, in some embodiments the cartridge may comprise a single-use cartridge, as disclosed in U.S. patent application Ser. No. 13/603,612, filed Sep. 5, 2012, which is incorporated herein by reference in its entirety.

In the exemplified embodiment, the control body 102 includes a control component 106 (e.g., a microcontroller), a flow sensor 108, and a battery 110, which can be variably aligned, and can include a plurality of indicators 112 at a distal end 114 of an outer body 116. The indicators 112 can be provided in varying numbers and can take on different shapes and can even be an opening in the body (such as for release of sound when such indicators are present). In the exemplified embodiment, a haptic feedback component 101 is included with the control component 106. As such, the haptic feedback component may be integrated with one or more components of a smoking article for providing vibration or like tactile indication of use or status to a user. See, for example, the disclosure of U.S. patent application Ser. No. 13/946,309, filed Jul. 19, 2013, which is incorporated herein by reference in its entirety.

An air intake 118 may be positioned in the outer body 116 of the control body 102. A coupler 120 also is included at the proximal attachment end 122 of the control body 102 and may extend into a control body projection 124 to allow for ease of electrical connection with an atomizer or a component thereof, such as a resistive heating element (described below) when the cartridge 104 is attached to the control body. Although the air intake 118 is illustrated as being provided in the outer body 116, in another embodiment the air intake may be provided in a coupler as described, for example, in U.S. patent application Ser. No. 13/841,233; Filed Mar. 15, 2013.

The cartridge 104 includes an outer body 126 with a mouth opening 128 at a mouthend 130 thereof to allow passage of air and entrained vapor (i.e., the components of the aerosol precursor composition in an inhalable form) from the cartridge to a consumer during draw on the aerosol delivery device 100. The aerosol delivery device 100 may be substantially rod-like or substantially tubular shaped or substantially cylindrically shaped in some embodiments. In other embodiments, further shapes and dimensions are encompassed—e.g., a rectangular or triangular cross-section, or the like.

The cartridge 104 further includes an atomizer 132 comprising a resistive heating element 134 (e.g., a wire coil) configured to produce heat and a liquid transport element 136 (e.g., a wick) configured to transport a liquid. Various embodiments of materials configured to produce heat when electrical current is applied therethrough may be employed to form the resistive heating element 134. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), and ceramic (e.g., a positive temperature coefficient ceramic). Further to the above, representative heating elements and materials for use therein are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties.

Electrically conductive heater terminals 138 (e.g., positive and negative terminals) at the opposing ends of the heating element 134 are configured to direct current flow through the heating element and configured for attachment to the appropriate wiring or circuit (not illustrated) to form an electrical connection of the heating element with the battery 110 when the cartridge 104 is connected to the control body 102. Specifically, a plug 140 may be positioned at a distal attachment end 142 of the cartridge 104. When the cartridge 104 is connected to the control body 102, the plug 140 engages the coupler 120 to form an electrical connection such that current controllably flows from the battery 110, through the coupler and plug, and to the heating element 134. The outer body 126 of the cartridge 104 can continue across the distal attachment end 142 such that this end of the cartridge is substantially closed with the plug 140 protruding therefrom.

A liquid transport element can be combined with a reservoir to transport an aerosol precursor composition to an aerosolization zone. In the embodiment shown in FIG. 1, the cartridge 104 includes a reservoir layer 144 comprising layers of nonwoven fibers formed into the shape of a tube encircling the interior of the outer body 126 of the cartridge, in this embodiment. An aerosol precursor composition is retained in the reservoir layer 144. Liquid components, for example, can be sorptively retained by the reservoir layer 144. The reservoir layer 144 is in fluid connection with a liquid transport element 136. The liquid transport element 136 transports the aerosol precursor composition stored in the reservoir layer 144 via capillary action to an aerosolization zone 146 of the cartridge 104. As illustrated, the liquid transport element 136 is in direct contact with the heating element 134 that is in the form of a metal wire coil in this embodiment.

It is understood that an aerosol delivery device that can be manufactured according to the present disclosure can encompass a variety of combinations of components useful in forming an electronic aerosol delivery device. Reference is made for example to the reservoir and heater system for controllable delivery of multiple aerosolizable materials in an electronic smoking article disclosed in U.S. Pat. App. Pub. No. 2014/0000638 to Sebastian et al., which is incorporated herein by reference in its entirety. Further, U.S. patent application Ser. No. 13/602,871, filed Sep. 4, 2012, discloses an electronic smoking article including a microheater, and which is incorporated herein by reference in its entirety.

Reference also is made to U.S. Pat. Pub. No. 2013/0213419, which discloses a ribbon of electrically resistive mesh material that may be wound around a wick, and to U.S. Pat. Pub. No. 2013/0192619, which discloses a heater coil about a wick wherein the coil windings have substantially uniform spacing between each winding. In certain embodiments according to the present disclosure, a heater may comprise a metal wire, which may be wound with a varying pitch around a liquid transport element, such as a wick. An exemplary variable pitch heater than may be used according to the present disclosure is described in U.S. patent application Ser. No. 13/827,994, filed Mar. 14, 2013, the disclosure of which is incorporated herein by reference in its entirety.

Reference also is made to a liquid supply reservoir formed of an elastomeric material and adapted to be manually compressed so as to pump liquid material therefrom, as disclosed in U.S. Pat. Pub. No. 2013/0213418. In certain embodiments according to the present disclosure, a reservoir may particularly be formed of a fibrous material, such as a fibrous mat or tube that may absorb or adsorb a liquid material.

In another embodiment substantially the entirety of the cartridge may be formed from one or more carbon materials, which may provide advantages in terms of biodegradability and absence of wires. In this regard, the heating element may comprise a carbon foam, the reservoir may comprise carbonized fabric, and graphite may be employed to form an electrical connection with the battery and controller. Such carbon cartridge may be combined with one or more elements as described herein for providing illumination of the cartridge in some embodiments. An example embodiment of a carbon-based cartridge is provided in U.S. Pat. U.S. App. Pub. No. 2013/0255702 to Griffith, Jr. et al., which is incorporated herein by reference in its entirety.

In use, when a user draws on the article 100, the heating element 134 is activated (e.g., such as via a flow sensor), and the components for the aerosol precursor composition are vaporized in the aerosolization zone 146. Drawing upon the mouthend 130 of the article 100 causes ambient air to enter the air intake 118 and pass through the central opening in the coupler 120 and the central opening in the plug 140. In the cartridge 104, the drawn air passes through an air passage 148 in an air passage tube 150 and combines with the formed vapor in the aerosolization zone 146 to form an aerosol. The aerosol is whisked away from the aerosolization zone 146, passes through an air passage 152 in an air passage tube 154, and out the mouth opening 128 in the mouthend 130 of the article 100.

The various components of an aerosol delivery device according to the present disclosure can be chosen from components described in the art and commercially available. Examples of batteries that can be used according to the disclosure are described in U.S. Pat. App. Pub. No. 2010/0028766, the disclosure of which is incorporated herein by reference in its entirety.

An exemplary mechanism that can provide puff-actuation capability includes a Model 163PC01D36 silicon sensor, manufactured by the MicroSwitch division of Honeywell, Inc., Freeport, Ill. Further examples of demand-operated electrical switches that may be employed in a heating circuit according to the present disclosure are described in U.S. Pat. No. 4,735,217 to Gerth et al., which is incorporated herein by reference in its entirety. Further description of current regulating circuits and other control components, including microcontrollers that can be useful in the present aerosol delivery device, are provided in U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., and U.S. Pat. No. 7,040,314 to Nguyen et al., all of which are incorporated herein by reference in their entireties.

Reference also is made to International Publications WO 2013/098396, WO 2013/098397, and WO 2013/098398, which describe controllers configured to control power supplied to a heater element from a power source as a means to monitor a status of the device, such as heater temperature, air flow past a heater, and presence of an aerosol forming material near a heater. In particular embodiments, the present disclosure provides a variety of control systems adapted to monitor status indicators, such as through communication of a microcontroller in a control body and a microcontroller or other electronic component in a cartridge component.

The aerosol precursor, which may also be referred to as an aerosol precursor composition or a vapor precursor composition, can comprise one or more different components. For example, the aerosol precursor can include a polyhydric alcohol (e.g., glycerin, propylene glycol, or a mixture thereof). Representative types of further aerosol precursor compositions are set forth in U.S. Pat. No. 4,793,365 to Sensabaugh, Jr. et al.; U.S. Pat. No. 5,101,839 to Jakob et al.; PCT WO 98/57556 to Biggs et al.; and Chemical and Biological Studies on New Cigarette Prototypes that Heat Instead of Burn Tobacco, R. J. Reynolds Tobacco Company Monograph (1988); the disclosures of which are incorporated herein by reference.

Still further components can be utilized in the aerosol delivery device of the present disclosure. For example, U.S. Pat. No. 5,154,192 to Sprinkel et al. discloses indicators that may be used with smoking articles; U.S. Pat. No. 5,261,424 to Sprinkel, Jr. discloses piezoelectric sensors that can be associated with the mouth-end of a device to detect user lip activity associated with taking a draw and then trigger heating; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. App. Pub. No. 2010/0163063 by Fernando et al. discloses identification systems for smoking devices; and WO 2010/003480 by Flick discloses a fluid flow sensing system indicative of a puff in an aerosol generating system; all of the foregoing disclosures being incorporated herein by reference in their entireties. Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,388,574 to Ingebrethsen; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. No. 8,156,944 to Hon; U.S. Pat. No. 8,365,742 to Hon; U.S. Pat. No. 8,375,957 to Hon; U.S. Pat. No. 8,393,331 to Hon; U.S. Pat. App. Pub. Nos. 2006/0196518 and 2009/0188490 to Hon; U.S. Pat. App. Pub. No. 2009/0272379 to Thorens et al.; U.S. Pat. App. Pub. Nos. 2009/0260641 and 2009/0260642 to Monsees et al.; U.S. Pat. App. Pub. Nos. 2008/0149118 and 2010/0024834 to Oglesby et al.; U.S. Pat. App. Pub. No. 2010/0307518 to Wang; WO 2010/091593 to Hon; WO 2013/089551 to Foo; and U.S. patent application Ser. No. 13/841,233, filed Mar. 15, 2013, each of which is incorporated herein by reference in its entirety. A variety of the materials disclosed by the foregoing documents may be incorporated into the present devices in various embodiments, and all of the foregoing disclosures are incorporated herein by reference in their entireties.

The foregoing description of use of the article can be applied to the various embodiments described herein through minor modifications, which can be apparent to the person of skill in the art in light of the further disclosure provided herein. The above description of use, however, is not intended to limit the use of the article but is provided to comply with all necessary requirements of disclosure of the present disclosure.

A further exemplary embodiment of a smoking article 200 (e.g., an aerosol delivery device) including a reservoir housing 244 that may be used with various embodiments according to the present disclosure is shown in FIG. 2. As illustrated therein, a control body 202 can be formed of a control body shell 201 that can include a control component 206, a flow sensor 208, a battery 210, and an LED 212. A cartridge 204 can be formed of a cartridge shell 203 enclosing the reservoir housing 244 that is in fluid communication with a liquid transport element 236 adapted to wick or otherwise transport an aerosol precursor composition stored in the reservoir housing to a heater 234. An opening 228 may be present in the cartridge shell 203 to allow for egress of formed aerosol from the cartridge 204. Such components are representative of the components that may be present in a cartridge and are not intended to limit the scope of cartridge components that are encompassed by the present disclosure. The cartridge 204 may be adapted to engage the control body 202 through a press-fit engagement between the control body projection 224 and the cartridge receptacle 240. Such engagement can facilitate a stable connection between the control body 202 and the cartridge 204 as well as establish an electrical connection between the battery 210 and control component 206 in the control body and the heater 234 in the cartridge. The cartridge 204 also may include one or more electronic components 250, which may include an IC, a memory component, a sensor, or the like. The electronic component 250 may be adapted to communicate with the control component 206.

In some embodiments, an electronic smoking article can comprise a hollow shell that is adapted to enclose one or more further elements of the device. The hollow shell may be a single unitary piece that includes all elements of the electronic smoking article. In two piece embodiments, such as described above, the hollow shell may relate to a cartridge shell or a control body shell.

Having now described several example embodiments of aerosol delivery devices that may be used with various example embodiments, several embodiments of a charging accessory device for an aerosol delivery device and related systems, methods, apparatuses, and computer program products for providing interactive services for aerosol delivery devices in accordance with the present disclosure will now be described. FIG. 3 illustrates a system 300 including a charging accessory device 304 for providing interactive services for aerosol delivery devices in accordance with some example embodiments of the present disclosure. The system 300 may include one or more of an aerosol delivery device 302, charging accessory device 304, computing device 306, network 308, or social networking service 310. It will be appreciated, however, that the components, devices or elements illustrated in and described with respect to FIG. 3 below may not be mandatory and thus some may be omitted in certain embodiments. Additionally, some embodiments may include further or different components, devices or elements beyond those illustrated in and described with respect to FIG. 3

The aerosol delivery device 302 may be embodied as any aerosol delivery device. By way of non-limiting example, in some embodiments, the aerosol delivery device 302 may comprise an embodiment of at least a portion of aerosol delivery device 100 or of smoking article 200.

The aerosol delivery device 302 may include a battery 312, which may be embodied as any battery or other power source that may be configured to supply power to provide for aerosol formation and/or other functionalities of aerosol delivery device 302. By way of non-limiting example, the battery 312 of some example embodiments may be an embodiment of battery 110 and/or battery 210. The battery 312 of some example embodiments is rechargeable, and may be embodied as any rechargeable battery or combination of rechargeable batteries. By way of non-limiting example, the battery 312 may comprise a lithium ion battery (e.g., a rechargeable lithium-manganese dioxide battery), lithium ion polymer battery, nickel-zinc battery, nickel-metal hydride battery, nickel cadmium battery, rechargeable alkaline battery, some combination thereof, and/or other type of rechargeable battery.

The aerosol delivery device 302 may further include a control component 314. The control component 314 may, for example, be at least partially embodied as a processor; microcontroller; integrated circuit; memory storing instructions executable by a processor, microcontroller, and/or other processing device; some combination thereof; or the like, which may be configured to monitor and/or control functionality of the aerosol delivery device 302. For example, in some embodiments, the control component 314 may comprise an embodiment of control component 106, control component 206, and/or electronic components 250.

The charging accessory device 304 may comprise a housing, which may define one or more receptacles configured to receive at least a portion of one or more aerosol delivery devices 302. In this regard, at least a portion of aerosol delivery device 302 may be releasably retained in the charging accessory device 302. For example, the housing of the charging accessory device 304 of some example embodiments may define a friction fit receptacle that may be configured to frictionally engage an outer shell of the aerosol delivery device 302, or portion thereof, such as a control body of the charging accessory device 304. As a further example, the housing of the charging accessory device 304 of some example embodiments may define a cavity enclosure that may be configured to enclose or otherwise retain the aerosol delivery device 302 through use of a retaining member, such as a latch, strap, door, and/or the like. In some example embodiments, the housing of charging accessory device 304 may further define one or more receptacles which may be configured to receive one or more cartridges, such as cartridge 104 and/or cartridge 204, which may be used with the aerosol delivery device 302.

It will be appreciated that the housing of the charging accessory device 304 may have any of a variety of form factors. In some example embodiments, the housing of the charging accessory device 304 may have a portable form factor such that the charging accessory device 304 may be carried in a pocket or handbag of a user. By way of non-limiting example, in some embodiments, the housing may have a size and shape substantially similar to that of a smart phone or pack of cigarettes.

FIG. 4 illustrates an example housing 400 of a charging accessory device in accordance with some example embodiments of the present disclosure. It will be appreciated, however, that the illustration of FIG. 4 is provided by way of non-limiting example to illustrate an example housing defining cavities to receive at least a portion of an aerosol delivery device and one or more cartridges in accordance with some example embodiments. As illustrated in FIG. 4, the housing 400 may define a receptacle 402, which may be configured to receive at least a portion of an aerosol delivery device 404. The at least a portion of the aerosol delivery device 404 may, for example, be an embodiment of at least a portion of aerosol delivery device 302. For example, in some embodiments, the receptacle 402 may be configured to receive a control body portion of an aerosol delivery device. As another example, in some embodiments, the receptacle 402 may be configured to receive a fully assembled aerosol delivery device comprising a control body portion and a cartridge that is ready to be used. In some example embodiments, the housing 400 may include one or more receptacles configured to receive a control body portion of an aerosol delivery device and one or more receptacles configured to receive a fully assembled aerosol delivery device comprising a control body portion and a cartridge. The housing 400 may further define one or more cartridge receptacles 408, which may be configured to receive cartridges for the aerosol delivery device 404.

In some example embodiments, the charging accessory device 302 may be configured to determine and provide an indication of a charge level of the battery 312 when the aerosol delivery device 302 (or portion thereof including the battery 312) is in a receptacle of the charging accessory device 302. For example, with reference to FIG. 4, the battery charge level indicator 406 may indicate a charge level of a battery of the aerosol delivery device 404 when inserted in or otherwise attached to receptacle 402.

In some example embodiments in which the housing of the charging accessory device 302 defines a receptacle configured to receive a cartridge, the charging accessory device 302 may be configured to determine and provide an indication of the level of aerosol precursor composition remaining in the cartridge. For example, with reference to FIG. 4, the example housing 400 may include an aerosol precursor composition level indicator 410 for each cartridge receptacle 408 and may indicate the level of aerosol precursor composition remaining in a cartridge inserted in or otherwise attached to the corresponding cartridge receptacle 408.

Returning to FIG. 3, the charging accessory device 304 may include a power storage device 322. The power storage device 322 may comprise a battery and/or other device that may be configured to store power that may be used to charge the battery 312 of the aerosol delivery device 302. In this regard, the charging accessory device 304 may further comprise a charging interface 324, which may be configured to establish an electrical connection between the power storage device 322 and the battery 312 when the aerosol delivery device 302 (or portion thereof) is inserted in a receptacle of the charging accessory device 304 and/or otherwise attached to the charging accessory device 304. In this regard, the charging interface 324 may be configured to supply power from the power storage device 324 to the battery 312 to charge the battery 312. For example, in some embodiments, the charging interface 324 may be configured to establish a physical connection to the battery 312 and/or other component of the aerosol delivery device 302. As another example, in some embodiments, the charging interface 324 may be configured to enable wireless charging of the battery 312 when the aerosol delivery device 302 is inserted in a receptacle of the charging accessory device 304 and/or otherwise within sufficient proximity of the charging accessory device 304.

The power storage device 322 may be rechargeable. In this regard, the power storage device 322 may comprise one or more rechargeable batteries and/or other rechargeable power storage devices. By way of non-limiting example, the power storage device 322 may include one or more rechargeable lithium ion batteries (e.g., a rechargeable lithium-manganese dioxide battery), one or more rechargeable lithium ion polymer batteries, one or more rechargeable nickel-zinc batteries, one or more rechargeable nickel-metal hydride batteries, one or more rechargeable nickel cadmium batteries, one or more rechargeable alkaline batteries, some combination thereof, and/or other type of rechargeable power storage device.

The charging accessory device 304 may further include an external power interface 326, which may be configured to support connection of the charging accessory device 304 to an external power source 328, which may supply power to charge the power storage device 322. The external power interface 326 may comprise any interface that may be used to interface with a power source and receive power from the power source. As such, the type of power source 328 that may be used may vary depending on the type(s) of external power interface 326 implemented on the charging accessory device 304. For example, in some embodiments, the external power interface 326 may include a Universal Serial Bus (USB) port or connector, which may be connected to a computing device, such as the computing device 306 of some example embodiments, which may be configured to supply power to the charging accessory device 304 that may be used to charge the power storage device 322. As such, the computing device 306 and/or other computing device 306 may provide the power source 328 in accordance with some example embodiments. As a further example, in some embodiments, the power source 328 may be embodied as an Alternating Current (AC)/Direct Current (DC) adapter (e.g., a wall charger), which may be configured to convert power from an AC electrical outlet to Direct Current (DC) that may be used to charge the power storage device 322. The AC/DC adapter may include a connector (e.g., a USB connector and/or other connector) and/or be configured to couple with a connector (e.g., a USB connector and/or other connector) that may be coupled with the external power interface 326.

If a power source 328 is coupled with the external power interface 326 while the aerosol delivery device 302 is not attached to the charging accessory device 304 (e.g., is not in a receptacle of the housing of the charging accessory device 304), the power source 38 may charge the power storage device 322. In some example embodiments, if a power source 328 is coupled with the external power interface 326 while the aerosol delivery device 302 is attached to the charging accessory device 304 (e.g., is in a receptacle of the housing of the charging accessory device 304), the power source 38 may recharge the power storage device 322, while the power storage device 322 recharges the battery 312.

In some example embodiments, the charging accessory device 304 may include one or more indicators, such as one or more LED indicators, a graphic display, and/or other user interface element, such as may be provided by the user interface 516 illustrated in and described further herein below with respect to FIG. 5, that may be used to indicate charging status and/or charging progress for the battery 312 and/or power storage device 322. For example, in some embodiments, the charging accessory may include a status indicator(s) that may be used to indicate whether the battery 312 is being charged (e.g., with power from the power storage device 322). As a further example, in some embodiments, the charging accessory may include a status indicator(s) that may be used to indicate whether the power storage device 322 is being charged (e.g., with power from power source 328). As another example, in some embodiments, such as that illustrated in FIG. 4, the charging accessory device 304 may include a battery charge level indicator that may indicate a charge level of the battery 312 and/or a charge level indicator that may indicate a charge level of the power storage device 322.

The charging accessory device 304 of some example embodiments may comprise an aerosol delivery device interface 334, which may be configured to establish a data connection between the charging accessory device 304 and the control component 314 and/or other element(s) of the aerosol delivery device 302 when the aerosol delivery device 302 (or portion thereof) is inserted in a receptacle of the charging accessory device 304 and/or otherwise attached to the charging accessory device 304. In this regard, the aerosol delivery device 334 may be configured to enable communication between the charging accessory device 304 and the control component 314 and/or other component(s) of the aerosol delivery device 302. It will be appreciated that the aerosol delivery device interface 334 may be implemented via any wired and/or wireless (e.g., Bluetooth, Zigbee, Wi-Fi direct, WLAN, and/or other wireless communication technology that may be used to interface two or more devices) interface that may be used to enable establishment of a data connection and communication between two devices. In some example embodiments, the charging interface 324 and aerosol delivery device interface 334 may be implemented via a shared interface that may be configured to carry both power and data, such as by way of non-limiting example, a USB interface.

In some example embodiments, the aerosol delivery device interface 334 may be configured to interface with a control body portion of the aerosol delivery device 302 via an interface and/or receptacle that may be used to receive a cartridge for use with the aerosol delivery device 302. In this regard, the aerosol delivery device interface 334 of some example embodiments may provide a data interface that may be inserted into a cartridge receptacle of a control body portion of the aerosol delivery device 302 in place of a cartridge (e.g., when the aerosol delivery device 302 is received to a receptacle, such as receptacle 402, of the charging accessory device 304). In some such embodiments, an input of the aerosol delivery device 302 that may be configured to read current sensing data may be used as a digital receive input, and an output that may be used for switching power to a heater element may be used as a digital output by the control component 314 to enable communication between the aerosol delivery device 302 and the charging accessory device 304. In this regard, heater connection points that may be used when a cartridge is inserted in the aerosol delivery device 302 may be repurposed to provide a serial interface between the aerosol delivery device 302 and charging accessory device 304.

The aerosol delivery device interface 334 may be used by the charging accessory device 304 to collect data from the aerosol delivery device 302. For example, in some embodiments, the charging accessory device 304 may be configured to collect usage data from the aerosol delivery device 302. In this regard, the control component 314 of some example embodiments may be configured to maintain usage data for the aerosol delivery device 302, which may be collected by the charging accessory device 304 via the aerosol delivery device interface 334. The charging accessory device 304 may be configured to at least temporarily store collected usage data on a memory that may be implemented on the charging accessory device 304, such as memory 514 illustrated in and described below with respect to FIG. 5.

The collected usage data may include any data detailing usage of the aerosol delivery device 302, such as, by way of non-limiting example, a number of cartridges used in the aerosol delivery device over a period of time, a number of puffs taken by the user over a period of time, total cumulative puff time (e.g., in seconds and/or other unit of time), average rest time between individual puffs, shortest observed rest time between individual puffs, longest observed rest time between individual puffs, total rest time between individual puffs (e.g., in seconds and/or other unit of time), a number of forced cutoffs for a puff exceeding a maximum allowable puff duration (e.g., 4 seconds), a number of smoking sessions for which the aerosol delivery device was used over a period of time, or a duration of one or more smoking sessions, a date/time of one or more smoking sessions, power consumption data, and/or other usage data. In some example embodiments in which a number of puffs taken by the user is captured, a double/triple/multi-clutch puff may be counted as a single puff. Additionally or alternatively, in some example embodiments, a double/triple/multi-cutch puff may be separately counted as individual puffs. As further examples, the usage data may include a total number of low cartridge warnings provided by the aerosol delivery device 302 over a period of time, a total number of empty cartridge errors provided by the aerosol delivery device 302 over a period of time, a total number of low battery warnings provided by the aerosol delivery device 302 over a period of time, a total number of empty battery errors provided by the aerosol delivery device 302 over a period of time, a total number of lockout occurrences over a period of time, and/or other status indications/warnings/errors that may be provided by the aerosol delivery device 302 during operation based on usage thereof. Usage data for a given period of time may be any time period, such as, by way of non-limiting example, a life of the aerosol delivery device 302, a time period elapsed since a previous charging of the aerosol delivery device 302 in the charging accessory device 304, or a time period specified by a user of the aerosol delivery device 302, charging accessory device 304, and/or computing device 306.

As a further example, the usage data may include a type(s) of aerosol precursor composition used in the aerosol delivery device 302. In this regard, a type of aerosol precursor composition may be defined at least in part by a chemical formulation of the aerosol precursor composition, a flavorant of the aerosol precursor composition, a brand of the aerosol precursor composition, a tobacco concentration of the aerosol precursor composition, and/or other qualities that may distinguish various types of aerosol precursor compositions.

In some embodiments, the charging accessory device 304 may be configured to collect diagnostic data from the aerosol delivery device 302. The diagnostic data may, for example, include data indicative of the functionality of one or more components of the aerosol delivery device 302, which may be used to identify any malfunctions, failed components, and/or other problems that may occur with the aerosol delivery device 302. As a further example, the diagnostic data may include a software version of software that may be installed on the aerosol delivery device 302. As another example, the diagnostic data may include a measured temperature (e.g., in degrees Fahrenheit and/or in degrees Celsius) of the aerosol delivery device 302 and/or one or more components thereof at a point of operation. For example, in some example embodiments, the diagnostic data may include an average measured temperature, minimum observed temperature, and/or maximum measured temperature at the start of the puff. The collected diagnostic data may be used to determine when a component of the aerosol delivery device 302 may need to be replaced and/or when software of the aerosol delivery device 302 should be updated.

The charging accessory device 304 may be further configured to track charging session data relating to one or more charging sessions. For example, the charging accessory device 304 may track a charge coulomb count for one or more charging sessions, a number of charger connections between the charging accessory device and aerosol delivery device 302, a charging time for a charging session, a total charging time over a period of time, a percentage of time in which the charging accessory device 304 was coupled with the charging accessory device that was used to charge the battery 312, and/or other charging session data.

In some example embodiments, the charging accessory device 304 may be configured to use the aerosol delivery device interface 334 to deliver a software update to the aerosol delivery device 302 to update a software configuration of the aerosol delivery device. For example, the software update may include a software upgrade, patch, and/or the like for operating software that may be implemented on the aerosol delivery device 302. As a further example, the software update may include an update (e.g., a customization) to one or more configuration settings of the aerosol delivery device 302, such as various operating parameters including a configuration of user interface functionality, such as functionality of an LED indicator(s) of the aerosol delivery device 302, a heating profile of the aerosol delivery device 302, an amount of aerosol precursor composition that is vaporized per puff, and/or other operating parameters of the aerosol delivery device 302. As another example, the software update may include personal information, such as a user name, address, contact information, and/or the like for a user of the aerosol delivery device 302, which may be programmed to the aerosol delivery device 302.

The charging accessory device 304 may further include a communication interface 336, which may be configured to enable communication between the charging accessory device 304 and one or more further devices and/or one or more networks. For example, the communication interface 336 may be configured to enable the charging accessory device 304 to communicate with the computing device 306 and/or to access the network 308. In this regard, the communication interface 336 may include one or more interface mechanisms for enabling communication with other devices and/or networks. As such, the communication interface 336 may include, for example, an antenna (or multiple antennas) and supporting hardware and/or software for enabling wireless communications with a wireless communication network and/or another device through a wireless communications technology, such as a cellular communication technology, Wi-Fi and/or other Institute of Electrical and Electronics Engineers (IEEE) 802.11 technology, Bluetooth, Zigbee, wireless USB, near field communication (NFC), radio frequency identification (RF-ID), WiMAX and/or other IEEE 802.16 technology, and/or other wireless communication technology. The communication interface 336 may additionally or alternatively include a communication modem or other hardware/software for supporting communication via cable, digital subscriber line (DSL), USB, FireWire, Ethernet, one or more optical transmission technologies, and/or other wireline networking methods. In some example embodiments, the external power interface 326 and communication interface 336 may be implemented via a shared interface that may be configured to carry both power and data, such as by way of non-limiting example, a USB interface.

The computing device 306 may be embodied as any computing device that may be configured to communicate with the charging accessory device 304 and access the network 308. By way of non-limiting example, the computing device 306 of some example embodiments may be embodied as a mobile computing device, such as a cellular telephone (e.g., a smartphone or other cellular telephone device), a tablet computing device, a digital media player, some combination thereof, or other mobile computing device. As a further example, the computing device 306 of some example embodiments may comprise a personal computer (PC), such as a desktop PC, laptop PC, or other type of PC.

The network 308 may be embodied as any network, or combination of networks, which may enable two or more computing devices to communicate with each other. In this regard, the network 308 may, for example, comprise one or more wireline networks, one or more wireless networks (e.g., a cellular network, WLAN, wireless metropolitan area network, wireless wide area network, some combination thereof, or the like), or a combination thereof, and in some example embodiments may comprise the Internet.

The computing device 306 and charging accessory device 304 may communicate via any wireless and/or wireline communication technology that may be supported by both the computing device 306 and the communication interface 336. For example, the computing device 306 and charging accessory device 304 may communicate via a USB connection, Firewire connection, Bluetooth, Zigbee, Wi-Fi direct, and/or other technology that may be used to interface two computing devices. Additionally or alternatively, in some example embodiments, the computing device 306 and charging accessory device 304 may be configured to communicate with each other via the network 308, or portion thereof, such as a local area network that may be used to access the network 308.

The computing device 306 may be further configured to access and communicate with the social networking service 310. The social networking service 310 may be implemented via one or more computing devices that may be configured to provide a social networking service comprising a community of aerosol delivery device users. By way of non-limiting example, the social networking service 310 may be implemented by one or more servers, a cloud computing infrastructure, and/or other computing device(s) that may be configured to provide a social networking service that may be accessed by computing devices, such as computing device 306, over the network 308.

In some example embodiments, the social networking service 310 may be a general purpose social networking service, such as Facebook, Twitter, LinkedIn, and/or the like, which may include a larger community of users, of which a subset may be aerosol delivery device users. As another example, in some embodiments, the social networking service 310 may be a dedicated social networking service for aerosol delivery devices, such as may be implemented and maintained by a manufacturer or vendor of one or more of the aerosol delivery device 302 or charging accessory device 304, a manufacturer or vendor of cartridges and/or other accessories for the aerosol delivery device 302, and/or other party that may be involved in the manufacture and/or distribution of aerosol delivery devices and/or aerosol delivery device accessories.

The computing device 306 may be configured to provide interactive services to enable a user to view and interact with data (e.g., usage data, diagnostic data, charging session data, and/or other data) about the aerosol delivery device 302 that may be provided by the charging accessory device 304 and/or social networking services that may be provided by the social networking service 310. For example, in some embodiments, the computing device 306 may implement a thin client, such as a web browser, dedicated thin client application, and/or the like which may be configured to enable a user to access and interact with the social networking service 310. As another example, in some embodiments, the computing device 306 may have an application, such as a mobile app, implemented thereon that may be configured to enable interaction with the aerosol delivery device 302, charging accessory device 304, and/or social networking service 310. In embodiments implementing a mobile app and/or other application, the application may be downloaded from an app store, the social networking service 310, a manufacturer or vendor of the aerosol delivery device 302, charging accessory device 304, and/or accessories for the aerosol delivery device 302.

The computing device 306 may be configured to receive and display data associated with the aerosol delivery device 302 that may be accessed and/or otherwise received from the charging accessory device 304. By way of non-limiting example, the data may include usage data (e.g., usage data that may be captured by the control component 312 and accessed by the charging accessory device 304 via the aerosol delivery device interface 334 as described above), diagnostic data that may be collected by the charging accessory device 304 as described above, a power level of the battery 312, charging session data (e.g., charging session data that may be captured by the charging accessory device 304 as described above), charging status of the battery 312, a power level of the power storage device 322, a charging status of the power storage device 322, a level of aerosol precursor composition remaining in a cartridge, and/or other data that may be captured and provided to the computing device 306 by the charging accessory device 304 of various example embodiments.

In some example embodiments, the computing device 306 may be configured to derive further data from data that may be received by the charging accessory device 304. For example, the computing device 306 of some example embodiments may be configured to derive a device usage pattern(s) for the aerosol delivery device 302 from usage data. The device usage pattern may include a favorite type of aerosol precursor composition used by a user of the aerosol delivery device 302, a time period during which the aerosol delivery device 302 is most commonly used, trends in usage of the aerosol delivery device 302, and/or other patterns that may be derived from usage data. As another example, the derived data may include a diagnosis of an operating condition of one or more components of the aerosol delivery device 302 that may be derived from diagnostic data.

In some example embodiments, social data may be generated based at least in part on usage data that may be collected by the charging accessory device 304. The social data may be sent to the social networking service 310 via the network 308. For example, in some embodiments, the social data may be included in a social media update, such as status update, tweet, post, and/or the like, that may be published to a social media account that may be associated with a user of one or more of the aerosol delivery device 302, charging accessory device 304, or computing device 306.

In some example embodiments, the computing device 306 may be configured to generate social data and send the social data to the social networking service. Additionally or alternatively, in some example embodiments, the charging accessory device 304 may be configured to generate social data and send the social data to the social networking service 310. In this regard, the charging accessory device 304 of various example embodiments may be configured to cause social data to be provided to the social networking service 310 by sending social data to the social networking service 310 and/or by providing usage data to a device, such as computing device 306 that may be configured to generate and send social data to the social networking service 310. Generation of social data and the provision of social data to the social networking service 310 in accordance with some example embodiments is described further herein below with respect to FIGS. 7 and 8.

The computing device 306 of some example embodiments may be further configured to receive and display social networking information and interactive services that may be provided by the social networking service 310. In this regard, the computing device 306 may be configured to enable user interaction with social networking services that may be provided by the social networking service 310. Several examples of such social networking services are described further herein below.

In some example embodiments, the charging accessory device 304 and/or computing device 306 may be configured to provide collected data (e.g., usage data, diagnostic data, charging session data, data derived therefrom, and/or other data) to a computing device that may be associated with a manufacturer or vendor of one or more of the aerosol delivery device 302 or charging accessory device 304, a manufacturer or vendor of cartridges and/or other accessories for the aerosol delivery device 302, and/or other party that may be involved in the manufacture and/or distribution of aerosol delivery devices and/or aerosol delivery device accessories. In this regard, collected data may be used by a manufacturer, vendor, and/or other interested party to diagnose any faults, adjust present and/or future aerosol delivery device configurations, and/or for other purposes.

Having now generally described elements and functionality of the system 300, several particular embodiments as well as additional functionality and services that may be provided by elements of the system 300 will be described below with respect to FIGS. 5-10.

FIG. 5 illustrates a block diagram of an apparatus 500 that may be implemented on a charging accessory device 304 in accordance with some example embodiments of the present disclosure. It will be appreciated that the components, devices or elements illustrated in and described with respect to FIG. 5 below may not be mandatory and thus some may be omitted in certain embodiments. Additionally, some embodiments may include further or different components, devices or elements beyond those illustrated in and described with respect to FIG. 5.

In some example embodiments, the apparatus 500 may include processing circuitry 510 that is configurable to perform and/or control performance of functions of the charging accessory device 304 in accordance with one or more example embodiments disclosed herein. Thus, the processing circuitry 510 may be configured to perform data processing, application execution and/or other processing and management services that may be implemented to perform functionality of the charging accessory device 304 according to one or more example embodiments.

In some embodiments, the apparatus 500 or a portion(s) or component(s) thereof, such as the processing circuitry 510, may include one or more chipsets, which may each include one or more chips. The processing circuitry 510 and/or one or more further components of the apparatus 500 may therefore, in some instances, be configured to implement an embodiment on a chipset.

In some example embodiments, the processing circuitry 510 may include a processor 512 and, in some embodiments, such as that illustrated in FIG. 5, may further include a memory 514. The processing circuitry 510 may be in communication with or otherwise control a user interface 516 and/or communication interface 518.

The processor 512 may be embodied in a variety of forms. For example, the processor 512 may be embodied as various hardware processing means such as a microprocessor, a coprocessor, a controller or various other computing or processing devices including integrated circuits such as, for example, an ASIC (application specific integrated circuit), an FPGA (field programmable gate array), some combination thereof, or the like. Although illustrated as a single processor, it will be appreciated that the processor 512 may comprise a plurality of processors. The plurality of processors may be in operative communication with each other and may be collectively configured to perform one or more functionalities of the charging accessory device 304. In some example embodiments, the processor 512 may be configured to execute instructions that may be stored in the memory 514 and/or that may be otherwise accessible to the processor 512. As such, whether configured by hardware or by a combination of hardware and software, the processor 512 may be capable of performing operations according to various embodiments while configured accordingly.

In some example embodiments, the memory 514 may include one or more memory devices. Memory 514 may include fixed and/or removable memory devices. In some embodiments, the memory 514 may provide a non-transitory computer-readable storage medium that may store computer program instructions that may be executed by the processor 512. In this regard, the memory 514 may be configured to store information, data, applications, instructions and/or the like for enabling the apparatus 500 to carry out various functions of the charging accessory device 304 in accordance with one or more example embodiments. For example, in some embodiments, memory 514 may be configured to at least temporarily store usage data, diagnostic data, and/or other data that may be collected from the aerosol delivery device 302. In some embodiments, the memory 514 may be in communication with one or more of the processor 512, user interface 516, or communication interface 518 via a bus (or buses) for passing information among components of the apparatus 500.

In some example embodiments, the apparatus 500 may further include the user interface 516. The user interface 516 may be in communication with the processing circuitry 510 to receive an indication of a user input and/or to provide an audible, visual, mechanical, or other output to a user. As such, the user interface 516 may include, for example, a keyboard, a display, a touch screen display, a microphone, a speaker, one or more indicator lights, and/or other input/output mechanisms. For example, the user interface 516 may comprise a display, one or more LEDs, and/or other output mechanisms that may be configured to indicate a charge level, charging status, and/or charging progress for one or more of the battery 312 or power storage device 322. As a further example, the user interface 516 may comprise a display, one or more LEDs, and/or other output mechanisms that may be configured to indicate a level of aerosol precursor composition remaining in one or more cartridges.

The apparatus 500 may further include a communication interface 518. The communication interface 518 may enable the apparatus 500 to communicate with one or more further computing devices 520, either directly, or via a network 522. The network 522 may comprise an embodiment of the network 308 and, as such, may include a local area network and/or a wide area network, such as the internet. The device(s) 520 may, for example, include an aerosol delivery device 302, computing device 306, social networking service 310, one or more further charging accessory devices 304, and/or other computing device with which the charging accessory device 304 may communicate. In this regard, the communication interface 518 may be configured to provide aspects of one or more of the aerosol delivery device interface 334 or communication interface 336. The communication interface 518 may accordingly include one or more interface mechanisms, such as an antenna (or multiple antennas) and supporting hardware and/or software for enabling communications via wireless communication technology (e.g., a cellular technology, communication technology, Wi-Fi and/or other IEEE 802.11 technology, Bluetooth, Zigbee, wireless USB, NFC, RF-ID, WiMAX and/or other IEEE 802.16 technology, and/or other wireless communication technology) and/or a communication modem or other hardware/software for supporting communication via cable, digital subscriber line (DSL), USB, FireWire, Ethernet, one or more optical transmission technologies, and/or other wireline networking methods.

FIG. 6 illustrates a block diagram of an apparatus 600 that may be implemented on a computing device, such as computing device 306, configured to provide interactive services for an aerosol delivery device, such as aerosol delivery device 302, in accordance with some example embodiments of the present disclosure. It will be appreciated that the components, devices or elements illustrated in and described with respect to FIG. 6 below may not be mandatory and thus some may be omitted in certain embodiments. Additionally, some embodiments may include further or different components, devices or elements beyond those illustrated in and described with respect to FIG. 6.

In some example embodiments, the apparatus 600 may include processing circuitry 610 that is configurable to perform functions in accordance with one or more example embodiments disclosed herein. In this regard, the processing circuitry 610 may be configured to perform and/or control performance of one or more functionalities of apparatus 600 (e.g., functionalities of the computing device 306) in accordance with various example embodiments. Thus, the processing circuitry 610 may be configured to perform data processing, application execution and/or other processing and management services according to one or more example embodiments.

In some embodiments, the apparatus 600 or a portion(s) or component(s) thereof, such as the processing circuitry 610, may include one or more chipsets, which may each include one or more chips. The processing circuitry 610 and/or one or more further components of the apparatus 600 may therefore, in some instances, be configured to implement an embodiment on a chipset.

In some example embodiments, the processing circuitry 610 may include a processor 612 and, in some embodiments, such as that illustrated in FIG. 6, may further include memory 614. The processing circuitry 610 may be in communication with or otherwise control a user interface 616, communication interface 618, and/or interactive services module 620.

The processor 612 may be embodied in a variety of forms. For example, the processor 612 may be embodied as various hardware processing means, such as a microprocessor, a coprocessor, a controller or various other computing or processing devices including integrated circuits such as, for example, an ASIC (application specific integrated circuit), an FPGA (field programmable gate array), some combination thereof, or the like. Although illustrated as a single processor, it will be appreciated that the processor 612 may comprise a plurality of processors. The plurality of processors may be in operative communication with each other and may be collectively configured to perform one or more functionalities of the apparatus 600. In some example embodiments, the processor 612 may be configured to execute instructions that may be stored in the memory 614 and/or that may be otherwise accessible to the processor 612. As such, whether configured by hardware or by a combination of hardware and software, the processor 612 may be capable of performing operations according to various embodiments while being configured accordingly.

In some example embodiments, the memory 614 may include one or more memory devices. Memory 614 may include fixed and/or removable memory devices. In some embodiments, the memory 614 may provide a non-transitory computer-readable storage medium that may store computer program instructions that may be executed by the processor 612. In this regard, the memory 614 may be configured to store information, data, applications, instructions and/or the like for enabling the apparatus 600 to carry out various functions in accordance with one or more example embodiments. In some embodiments, the memory 614 may be in communication with one or more of the processor 612, user interface 616, communication interface 618, or interactive services module 620 via a bus (or buses) for passing information among components of the apparatus 600.

In some example embodiments, the apparatus 600 may include the user interface 616. The user interface 616 may be in communication with the processing circuitry 610 to receive an indication of a user input and/or to provide an audible, visual, mechanical, or other output to a user. As such, the user interface 616 may include, for example, a keyboard, a mouse, a joystick, a display, a touch screen display, a microphone, a speaker, one or more biometric input devices (e.g., a visual or sensorial tracing device that may track body part or eye movements), and/or other input/output mechanisms. The user interface 616 of some example embodiments may be used by a user to view data associated with the aerosol delivery device 302 that may be provided by and/or otherwise derived from data that may be provided by the charging accessory device 304. The user interface 616 may additionally or alternatively be used by a user to interact with social networking services that may be provided by the social networking service 310 of some example embodiments.

The apparatus 600 may further comprise the communication interface 618. The communication interface 618 may enable the apparatus 600 to communicate with one or more further computing devices 620, either directly, or via a network 622. In this regard, the communication interface 618 may include one or more interface mechanisms for enabling communication with other devices and/or networks. The network 622 may comprise an embodiment of the network 308 and, as such, may include a local area network and/or a wide area network, such as the internet. The device(s) 620 may, for example, include an aerosol delivery device 302, charging accessory device 304, social networking service 310, and/or other computing device with which the computing device 306 may communicate. The communication interface 618 may accordingly include one or more interface mechanisms, such as an antenna (or multiple antennas) and supporting hardware and/or software for enabling communications via wireless communication technology (e.g., a cellular technology, communication technology, Wi-Fi and/or other IEEE 802.11 technology, Bluetooth, Zigbee, wireless USB, NFC, RF-ID, WiMAX and/or other IEEE 802.16 technology, and/or other wireless communication technology) and/or a communication modem or other hardware/software for supporting communication via cable, digital subscriber line (DSL), USB, FireWire, Ethernet, one or more optical transmission technologies, and/or other wireline networking methods.

The apparatus 600 may further include interactive services module 620. The interactive services module 620 may be embodied as various means, such as circuitry, hardware, a computer program product comprising computer readable program instructions stored on a computer readable medium (for example, the memory 614) and executed by a processing device (for example, the processor 612), or some combination thereof. In some embodiments, the processor 612 (or the processing circuitry 610) may include, or otherwise control, the interactive services module 620. The interactive services module 620 may be configured to provide interactive services for enabling interaction with the aerosol delivery device 302, charging accessory device 304 and/or with the social networking service 310. For example, the interactive services module 620 may be configured to process data that may be received from the charging accessory device 304, such as to derive further data, generate social data, and/or the like. As a further example, the interactive services module 620 may be configured to provide a graphical user interface, such as may be viewed on a display of the user interface 616 to enable a user to view data associated with aerosol delivery device 302, update a software configuration of the aerosol delivery device 302 (e.g., via the charging accessory device 304), interact with social networking services that may be provided by the social networking service 310, and/or the like. In some example embodiments, one or more aspects of the interactive services module 620 may be provided by an application, such as a mobile app, that may be stored on memory 614 and executed by the processor 612.

FIG. 7 illustrates a flowchart according to an example method that may be performed by the charging accessory device 302 to collect and provide access to usage data for the aerosol delivery device 302 to the computing device 306 for use in providing interactive services in accordance with some example embodiments of the present disclosure. One or more of aerosol delivery device interface 334, communication interface 336, processing circuitry 510, processor 512, memory 514, user interface 516, or communication interface 518 may, for example, provide means for performing one or more of the operations illustrated in and described with respect to FIG. 7.

Operation 700 may include the charging accessory device 302 communicating with the control component 314 of the aerosol delivery device 302 to access usage data for the aerosol delivery device 302. This usage data may include any data related to usage of the aerosol delivery device 302, such as, by way of non-limiting example, a number of cartridges used in the aerosol delivery device over a period of time, a number of puffs taken by the user over a period of time, a total cumulative puff time over a period of time, a number of smoking sessions for which the aerosol delivery device was used over a period of time, or a duration of one or more smoking sessions, a date/time of one or more smoking sessions, power consumption data, and/or other usage data described herein. As a further example, the usage data may include a type(s) of aerosol precursor composition used in the aerosol delivery device 302.

Operation 710 may include the charging accessory device 304 providing the usage data to the computing device 306. In some example embodiments, one or more of operations 700 or 710 may be performed in response to a request from the computing device 306. Additionally or alternatively, in some example embodiments, the charging accessory device 304 may be configured to automatically provide collected usage data to the computing device 306 when a communication channel between the charging accessory device 304 and the computing device 306 is available.

FIG. 8 illustrates a flowchart according to an example method for providing social data generated based at least in part on aerosol delivery device usage data provided by the charging accessory device 304 to the social networking service 310 in accordance with some example embodiments of the present disclosure. More particularly, FIG. 8 illustrates a method that may be performed by computing device 306 based on usage data that may be provided by the charging accessory device 304 attendant to performance of operations 700-710 as described above. One or more of processing circuitry 610, processor 612, memory 614, user interface 616, communication interface 618, or interactive services module 620 may, for example, provide means for performing one or more of the operations illustrated in and described with respect to FIG. 8.

Operation 800 may include the computing device 306 receiving usage data for the aerosol delivery device 302 from the charging accessory device 304. In this regard, operation 800 may comprise the computing device 306 receiving usage data that may be provided to the computing device 306 attendant to performance of operation 710.

Operation 810 may include the computing device 306 generating social data based at least in part on the usage data. For example, in some embodiments, operation 810 may include generating social data that may be included in a social media update that may be published to a social network account associated with a user of the aerosol delivery device 302.

It will be appreciated that the social data that may be generated in operation 810 may include any of a variety of elements of usage data that may be collected from the aerosol delivery device 302. For example, if the usage data includes a type of aerosol precursor composition used in the aerosol delivery device, the social data may indicate that the user smoked the type of aerosol precursor composition. As another example, the social data may indicate various usage statistics that may be derived from usage data, such as one or more of the number of cartridges used in the aerosol delivery device 302 over a period of time, the number of puffs taken by the user over a period of time, total cumulative puff time over a period of time, the number of smoking sessions for which the aerosol delivery device 302 was used over a period of time, or the duration of one or more smoking sessions.

As a further example, in some embodiments, the computing device 306 may be configured to derive a device usage pattern(s) for the aerosol delivery device 302 from usage data that may be received in operation 800. In such example embodiments, the social data that may be generated in operation 810 may include an indication of the derived usage pattern.

In some example embodiments, the computing device 306 may be configured to determine a location of the computing device 306 and generate the social data to include an indication of the location. For example, the location may be determined through a satellite navigation system, such as the Global Positioning System (GPS) and/or other satellite navigation system, location services that may be provided by a cellular network, location information that may be obtained from a wireless local area network (WLAN) access point, and/or other source of location information that may be used to at least approximate the location of the computing device 306.

Operation 820 may include the computing device 306 sending the social data to the social networking service 310. For example, in some embodiments, operation 820 may include sending the social data to the social networking service 310 for use by the social networking service 310 to provide social networking services, loyalty rewards (e.g., coupons), and/or other services to a user of the aerosol delivery device 302. Additionally or alternatively, in some example embodiments, operation 820 may include causing a social media update comprising the social data to be published to social network account associated with a user of the aerosol delivery device 302.

In some example embodiments, the social networking service 310 may be configured to provide social networking services to the computing device 306 based at least in part on social data that may be sent to the social networking service 310. For example, in some example embodiments, the social networking service 310 may be configured to facilitate the identification of nearby aerosol delivery device users with which the user may socialize. In this regard, the computing device 306 of some example embodiments may be configured to provide a location of the user of the aerosol delivery device 302 to the social networking service 310, such as in social data as described above and/or in a dedicated location update message, and the social networking service 310 may be configured to identify other aerosol delivery device users that are members of the social networking service 310 who are proximate to the location of the user of the aerosol delivery device 302. Nearby aerosol delivery device users may, for example, be users within a defined distance of the location of the user of the aerosol delivery device 302. The defined distance may, for example, be a distance defined by the social networking service 310 and/or a distance that may be selected by the user of the aerosol delivery device 302, such as through interaction with the computing device 306.

In some example embodiments, the social networking service 310 may identify existing contacts (e.g., friends) of the user on the social networking service 310 that are nearby to the user's location. Additionally or alternatively, in some example embodiments, the social networking service 310 may identify nearby aerosol delivery device users that are not existing contacts of the user of the aerosol delivery device 302. For example, in some embodiments, the social networking service 310 may identify nearby aerosol delivery device users that may have a similar device usage pattern to that of the user of the aerosol delivery device 302.

The social networking service 310 may provide an indication of one or more identified aerosol delivery device users that are nearby the location of the user of the aerosol delivery device 302 to the computing device 306. The computing device 306 may be configured to display an indication of at least one of the nearby aerosol delivery device users indicated by the social networking service 310 along with associated location information for the nearby aerosol delivery device user(s). For example, the indication may be displayed within a graphical user interface of an application that may be used to access the social networking service 310. In some example embodiments, display of an indication of a nearby aerosol delivery device user may include displaying an indication of the location of the nearby aerosol delivery device user on a map. As another example, in some embodiments, display of an indication of a nearby aerosol delivery device user may include listing a name of the nearby aerosol delivery device user along with location information, such as a name (e.g., a store name, restaurant name, and/or the like) and/or address of the location of the nearby aerosol delivery device user.

In some example embodiments, the social networking service 310 may be configured to identify an aerosol delivery device user on the social networking service 310 having a device usage pattern correlating to social data sent to the social networking service 310 by the computing device 306 and/or by the charging accessory device 304. As described above, in some embodiments, the social data may directly indicate a device usage pattern. Additionally or alternatively, in some example embodiments, the social networking service 310 may be configured to derive a device usage pattern for the user of the aerosol delivery device 302 based on social media updates that may be published to the user's account and/or based on other social data that may be sent to the social networking service 310, which may be indicative of usage of the aerosol delivery device 302 by the user. A user having a device usage pattern correlating to a device usage pattern for the user of the aerosol delivery device 302 may have an identical device usage pattern and/or may have a device usage pattern exhibiting similarities within a comparison threshold that may be applied to determine whether two device usage patterns are correlated. The social networking service 310 may be further configured to provide an indication of an aerosol delivery device user having an aerosol delivery device usage pattern correlating to a device usage pattern of the user of the aerosol delivery device 302 to the computing device 306. The computing device 306 may be configured to present the aerosol delivery device user as a suggested contact on the social networking service 310 for the user of the aerosol delivery device 302. For example, the computing device 306 may be configured to display an indication of the suggested contact within a graphical user interface of an application that may be used to access the social networking service 310.

In some example embodiments, a user of the computing device 306 may be presented with electronic coupons selected based at least in part on usage data received from the charging accessory device 304 and/or on social data sent to the social networking service 310. In some such example embodiments, an electronic coupon presented to the user may be selected by the computing device 306 from a plurality of available options. Additionally or alternatively, in some example embodiments, the coupon may be selected by the social networking service 310 and provided to the computing device 306 so that the electronic coupon may be presented to the user. For example, if usage data and/or social data indicate that a user prefers a certain type of aerosol precursor composition, an electronic coupon may be presented for cartridges containing the preferred aerosol precursor composition and/or for cartridges containing a comparable aerosol precursor composition. As another example, if a user is located within proximity of a store selling cartridges and/or other accessories for the aerosol delivery device 302, an electronic coupon for use in that store may be presented. As a further example, in some embodiments, a user may be presented with a loyalty coupon for participating in the social networking service 310, such as by publishing a defined number of social media updates related to usage of the aerosol delivery device 302 to his or her account.

As discussed previously, in some example embodiments, a software configuration of the aerosol delivery device 302 may be updated by the charging accessory device 304. The software configuration update may, for example, include a software configuration of the control component 314 and/or may include a software configuration update that may define and/or adjust an operating parameter of a cartridge that may be used in the aerosol delivery device 302. In some such example embodiments, the software update may be provided to the charging accessory device 304 by the computing device 306. Additionally or alternatively, in some example embodiments, the computing device 306 may be configured to communicate directly with the aerosol delivery device 302 to provide a software configuration update to the aerosol delivery device 302.

In some embodiments, the computing device 306 may download a software update from a source over the network 308, such as from social networking service 310, from a manufacturer of the aerosol delivery device 302 and/or component thereof, from a vendor of the aerosol delivery device 302 and/or component thereof, and/or from some other source that may provide software updates for the aerosol delivery device 302. The computing device 306 may send the software update to the charging accessory device 304 so that the charging accessory device 304 may use the software update to update the software configuration of the aerosol delivery device 302.

Additionally or alternatively, in some example embodiments, the computing device 306 (e.g., the interactive services module 620) may be configured to provide an interface enabling a user to select a configuration setting update for the aerosol delivery device 302. For example, in some embodiments, a user interface may enable a user to select to adjust and/or otherwise update to one or more configurations of the aerosol delivery device 302. It will be appreciated that such configuration update may include an adjustment to any adjustable configuration of the aerosol delivery device 302, such as by way of example, a heating profile configuration, a configuration for operation of one or more LEDs and/or other user interface element(s) that may be implemented on the aerosol delivery device 302, an amount of aerosol precursor vaporized per puff, a configuration relating to charging of the battery 312, a configuration regulating consumption of the battery 312, and/or the like. The computing device 306 may generate a software update including the selected configuration setting update and send the generated software update to the charging accessory device 304. Example methods according to such example embodiments are illustrated in and described below with respect to FIGS. 9 and 10. FIG. 9 illustrates a flowchart according to an example method for providing a software update for an aerosol delivery device to the charging accessory device 304 in accordance with some example embodiments of the present disclosure. In this regard, FIG. 9 illustrates a method that may be performed by the computing device 306 in accordance with some example embodiments. One or more of processing circuitry 610, processor 612, memory 614, user interface 616, communication interface 618, or interactive services module 620 may, for example, provide means for performing one or more of the operations illustrated in and described with respect to FIG. 9.

Operation 900 may include the computing device 306 receiving an indication of a selected configuration setting update for the aerosol delivery device 302. For example, the indication may be received via a graphical user interface that may be displayed by the computing device 306, such as under the control of the interactive services module 620. The selected configuration setting update may include an update to any configuration setting of the aerosol delivery device 302. By way of non-limiting example, the configuration setting update may update various operating parameters, such as functionality of an LED indicator(s) of the aerosol delivery device 302, a heating profile of the aerosol delivery device 302, an amount of aerosol precursor composition that is vaporized per puff, and/or other operating parameters of the aerosol delivery device 302.

Operation 910 may include the computing device 306 generating a software update including the selected configuration setting update. Operation 920 may include the computing device 306 sending the software update to the charging accessory device.

FIG. 10 illustrates a flowchart according to an example method that may be performed by the charging accessory device 304 to update a software configuration of the aerosol delivery device 302 in accordance with some example embodiments of the present disclosure. More particularly, FIG. 10 illustrates an example method that may be performed by the charging accessory device 304 to update the software configuration of the aerosol delivery device 302 with a software update that may be provided by the computing device 306 attendant to performance of the method of FIG. 9. One or more of aerosol delivery device interface 334, communication interface 336, processing circuitry 510, processor 512, memory 514, user interface 516, or communication interface 518 may, for example, provide means for performing one or more of the operations illustrated in and described with respect to FIG. 10.

Operation 1000 may include the charging accessory device 304 receiving a software update from the computing device 306. For example, the received software update may be a software update that may be provided by the computing device 306 attendant to performance of operation 920 as described above.

Operation 1010 may include the charging accessory device 304 using the software update to update a software configuration of the aerosol delivery device 302. Update of the software configuration may include updating a software configuration of any component of the aerosol delivery device 302, including, for example, the control component 314, a cartridge, and/or other component.

In some example embodiments, a software configuration update may be provided to the aerosol delivery device 302 by the social networking service 310. For example, in some such embodiments, the social networking service 310 may communicate the software configuration update to the aerosol delivery device 302 via the network 308. Additionally or alternatively, in some example embodiments, a software configuration update may be propagated from the social networking service 310 to the aerosol delivery device 302 via one or more intermediate devices, such as computing device 306 and/or charging accessory device 304. A software configuration update that may be provided by the social networking service 310 may comprise a software update for software that may be implemented on the aerosol delivery device 302. Additionally or alternatively, a software configuration update that may be provided by the social networking service 310 may and/or may adjust a configuration of the aerosol delivery device 302, such as by way of example, a heating profile configuration, a configuration for operation of one or more LEDs and/or other user interface element(s) that may be implemented on the aerosol delivery device 302, a configuration relating to charging of the battery 312, a configuration regulating consumption of the battery 312, and/or the like.

In some example embodiments in which the social networking service 310 may provide a software configuration update to the aerosol delivery device 302, the social networking service 310 may provide an interface, such as may be accessible by the computing device 306 and/or by another computing device over the network 308. The interface may enable a user to adjust one or more configurations of the aerosol delivery device 302. The social networking service 310 may generate a software configuration update based on user-selected adjustments and may provide the software configuration update to the aerosol delivery device 302, either directly via network 308 or indirectly via one or more intermediate devices, such as computing device 306 and/or charging accessory device 304.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. A system for providing interactive services for aerosol delivery devices, the system comprising:
at least a portion of an aerosol delivery device, comprising:
a control component configured to maintain usage data for the aerosol delivery device; and
a battery;
a computing device configured to access a network and communicate with a social networking service comprising a community of aerosol delivery device users; and
a charging accessory device comprising:
a power storage device; and
a communication interface configured to enable communication between the charging accessory device and the computing device,
wherein the charging accessory device is configured to:
supply power from the power storage device to the battery to charge the battery; and
communicate with the control component to access the usage data and wherein the computing device is further configured to:
receive the usage data from the charging accessory device;

derive a device usage pattern from the usage data;
generate social data based at least in part on the usage data, the social data including an indication of the device usage pattern; and
send the social data to the social networking service, wherein the charging accessory device is further configured to receive a software update, via the communication interface, for the aerosol delivery device and execute the software update to update a software configuration of the aerosol delivery device in communication with the charging accessory device, the software update being a software revision to a current software version implemented on the aerosol delivery device and including a software configuration update selected from the group consisting of: an update to a configuration of a heating profile of the aerosol delivery device in relation to an amount of heat produced by a heating element of the aerosol delivery device, an update to an amount of aerosol precursor composition vaporized per puff of the aerosol delivery device, and an update to a functionality of a user interface of the aerosol delivery device.

2. The system of claim 1, wherein the computing device is configured to send the social data to the social networking service at least in part by causing a social media update comprising the social data to be published to an account associated with a user of the aerosol delivery device.

3. The system of claim 2, wherein:
the usage data comprises a type of aerosol precursor composition used in the aerosol delivery device; and
the social media update indicates that the user smoked the type of aerosol precursor composition.

4. The system of claim 2, wherein:
the usage data comprises one or more of a number of cartridges used in the aerosol delivery device over a period of time, a number of puffs taken by the user over the period of time, a total cumulative puff time over the period of time, a number of smoking sessions for which the aerosol delivery device was used over the period of time, or a duration of one or more smoking sessions; and
the social media update indicates at least one of the one or more of the number of cartridges used in the aerosol delivery device over the period of time, the number of puffs taken by the user over the period of time, the total cumulative puff time over the period of time, the number of smoking sessions for which the aerosol delivery device was used over the period of time, or the duration of one or more smoking sessions.

5. The system of claim 1, wherein the computing device is further configured to: determine a location of the computing device; and
generate the social data to include an indication of the location.

6. The system of claim 1, wherein the computing device is further configured to present an electronic coupon selected based at least in part on one or more of the usage data or the social data.

7. The system of claim 1, wherein the computing device is further configured to: provide a location of a user of the aerosol delivery device to the social networking service;
receive an indication from the social networking service of one or more aerosol delivery device users located within a defined distance of the location of a user of the aerosol delivery device; and
display an indication of at least one of the one or more aerosol delivery device users with associated location information for each of the at least one of the one or more aerosol delivery device users.

8. The system of claim 1, wherein the computing device is further configured to: receive, from the social networking service, an indication of an aerosol delivery device user having an aerosol delivery device usage pattern correlating to the social data; and
present the aerosol delivery device user having the aerosol delivery device usage pattern correlating to the social data as a suggested contact on the social networking service.

9. The system of claim 1, wherein the computing device is further configured to: receive an indication of a selected configuration setting update for the aerosol delivery device; and
generate the software update to include the selected configuration setting update.

10. The system of claim 1 further comprising a housing defining a receptacle configured to engage with the at least a portion of the aerosol delivery device, wherein:
the housing further defines a second receptacle configured to engage with a cartridge;
the charging accessory device is further configured to determine a level of aerosol precursor composition remaining in the cartridge and to provide an indication of the level of aerosol precursor composition remaining in the cartridge to the computing device; and
the computing device is further configured to display the level of aerosol precursor composition remaining in the cartridge.

11. The system of claim 1, wherein the computing device is a mobile computing device.

12. The system of claim 1, wherein the computing device is configured to communicate with a second computing device via the network, and
wherein the usage data includes usage and diagnostic data, and the computing device is further configured to transmit the usage and diagnostic data to the second computing device for use to diagnose any faults of the aerosol delivery device, or adjust a present or future configuration of the aerosol delivery device.

13. The system of claim 1, wherein the computing device is further configured to receive the software update for the aerosol delivery device, directed thereto from the social networking service, the computing device being further configured to direct the software update to the charging accessory device for execution.

14. A charging accessory device, comprising:
a housing configured to engage with at least a portion of an aerosol delivery device comprising a battery;
a power storage device;
a charging interface configured to establish an electrical connection with the battery and supply electrical power from the power storage device to the battery to charge the battery;
an aerosol delivery device interface configured to enable communication between the charging accessory device and a control component of the aerosol delivery device;
a communication interface; and
processing circuitry configured to control the charging accessory device to at least:
access usage data for the aerosol delivery device via the aerosol delivery device interface; and
cause, via the communication interface, social data generated based at least in part on the usage data to be provided to a social networking service comprising a community of aerosol delivery device users, the social data including an indication of a device usage pattern derived from the usage data, wherein the processing circuitry is configured to control the charging accessory device to cause the social data to be provided to the social networking service at least in part by causing the charging accessory device to provide the usage data to a computing device configured to interface with the social networking service, wherein the charging accessory device is further configured to receive a software update, via the communication interface, for the aerosol delivery device and execute the software update to update a software configuration of the aerosol delivery device in communication with the charging accessory device, the software update being a software revision to a current software version implemented on the aerosol delivery device and including a software configuration update selected from the group consisting of: an update to a configuration of a heating profile of the aerosol delivery device in relation to an amount of heat produced by a heating element of the aerosol delivery device, an update to an amount of aerosol precursor composition vaporized per puff of the aerosol delivery device, and an update to a functionality of a user interface of the aerosol delivery device.

15. The charging accessory device of claim 14, wherein the processing circuitry is configured to control the charging accessory device to cause the social data to be provided to the social networking service at least in part by causing the charging accessory device to send the social data to the social networking service via a network.

16. The charging accessory device of claim 14, wherein the usage data comprises one or more of a type of aerosol precursor composition used in the aerosol delivery device, a number of cartridges used in the aerosol delivery device over a period of time, a number of puffs taken by a user of the aerosol delivery device over the period of time, a total cumulative puff time over the period of time, a number of smoking sessions for which the aerosol delivery device was used over the period of time, or a duration of one or more smoking sessions.

17. The charging accessory device of claim 14, wherein the processing circuitry is further configured to control the charging accessory device to update a software configuration of the aerosol delivery device.

18. The charging accessory device of claim 14, further comprising:
an external power interface configured to receive power to recharge the power storage device when coupled with an external power source.

19. The charging accessory device of claim 14, wherein the usage data includes usage and diagnostic data, and the processing circuitry is further configured to control the charging accessory device to:
cause, via the communication interface, the usage and diagnostic data to be provided to a computing device for use to diagnose any faults of the aerosol delivery device, or adjust a present or future configuration of the aerosol delivery device.

20. The charging accessory device of claim 14, wherein the computing device is further configured to receive the software update for the aerosol delivery device, directed thereto from the social networking service, the computing device being further configured to direct the software update to the charging accessory device for execution.

21. A method for providing interactive services for aerosol delivery devices, the method comprising a computing device:
establishing communication with a charging accessory device for an aerosol delivery device;
receiving usage data for the aerosol delivery device provided by the charging accessory device;
deriving a device usage pattern from the usage data;
generating social data based at least in part on the usage data, the social data including an indication of the device usage pattern; and
sending the social data to a social networking service comprising a community of aerosol delivery device users;
wherein the charging accessory device is further configured to receive a software update, via a communication interface of the charging accessory device, for the aerosol delivery device and execute the software update to update a software configuration of the aerosol delivery device in communication with the charging accessory device, the software update being a software revision to a current software version implemented on the aerosol delivery device and including a software configuration update selected from the group consisting of: an update to a configuration of a heating profile of the aerosol delivery device in relation to an amount of heat produced by a heating element of the aerosol delivery device, an update to an amount of aerosol precursor composition vaporized per puff of the aerosol delivery device, and an update to a functionality of a user interface of the aerosol delivery device.

22. The method of claim 21, wherein sending the social data to the social networking service comprises causing a social media update comprising the social data to be published to an account associated with a user of the aerosol delivery device.

23. The method of claim 21, wherein the usage data includes usage and diagnostic data, and the method further comprises:
sending the usage and diagnostic data to a computing device for use to diagnose any faults of the aerosol delivery device, or adjust a present or future configuration of the aerosol delivery device.

24. The method of claim 21 further comprising the computing device receiving the software update for the aerosol delivery device, directed thereto from the social networking service, and the computing device directing the software update to the charging accessory device for execution.

* * * * *